US008110551B2

(12) United States Patent
Shenker et al.

(10) Patent No.: US 8,110,551 B2
(45) Date of Patent: Feb. 7, 2012

(54) CYTOLETHAL DISTENDING TOXIN AND USE THEREOF

(75) Inventors: Bruce Shenker, Haverford, PA (US); Kathleen Boesze-Battaglia, Haddon Heights, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/357,471

(22) Filed: Jan. 22, 2009

(65) Prior Publication Data

US 2009/0202592 A1 Aug. 13, 2009

Related U.S. Application Data

(60) Provisional application No. 61/006,557, filed on Jan. 22, 2008.

(51) Int. Cl.
*A61K 38/00* (2006.01)

(52) U.S. Cl. .................... 514/21.2; 514/19.2; 424/278.1

(58) Field of Classification Search ........................ None
See application file for complete search history.

(56) References Cited

U.S. PATENT DOCUMENTS

2005/0032217 A1* 2/2005 Zadeh .......................... 435/455

OTHER PUBLICATIONS

Shenker et al (J. Immunol. 167:435-441, 2001).*
Ohara et al (Infection and Immunity, 72(2):871-879, 2004).*
Wising et al (Toxicon 45:767-776, 2005).*
Shenker et al (J. Immunol., 172:410-417, 2004).*

* cited by examiner

*Primary Examiner* — Patricia A Duffy
(74) *Attorney, Agent, or Firm* — Mark S. Cohen; Pearl Cohen Zedek Latzer, LLP

(57) ABSTRACT

This invention relates to immunotoxins and their use. Specifically, the invention relates to compositions comprising Cdt toxins or their inhibitors and their use in methods for treating infectious and proliferative diseases.

4 Claims, 11 Drawing Sheets

CYTOLETHAL DISTENDING TOXIN AND USE THEREOF

CROSS REFERENCE TO RELATED APPLICATIONS

This application claims the benefit of U.S. Application Ser. No. 61/006,557, filed on Jan. 22, 2008, which is herein incorporated by reference in its entirety.

GOVERNMENT INTEREST STATEMENT

This invention was made in whole or in part with government support under the U.S. Public Health Service Grant Number DE06014 to Dr. Bruce J. Shenker. The government may have certain rights in the invention.

FIELD OF INVENTION

This invention is directed to immunotoxins and their use. Specifically, the invention relates to compositions comprising Cdt toxins or their inhibitors and their use in methods for treating infectious and proliferative diseases.

BACKGROUND OF THE INVENTION

The cytolethal distending toxins are a family of heat-labile protein cytotoxins produced by several different bacterial species including diarrheal disease-causing enteropathogens such as some *Escherichia coli isolates, Campylobacter jejuni, Shigella* species, *Haemophilus ducreyi* and *Actinobacillus actinomycetemcomitans*. There is clear evidence that Cdts are encoded by three genes, designated CdtA, CdtB, and CdtC which are arranged as an apparent operon. These three genes specify three polypeptides designated CdtA, CdtB and CdtC with apparent molecular masses of 28, 32 and 20 kDa, respectively, that form a heterotrimeric holotoxin. Several cell lines and cell types have been shown to be sensitive to Cdt; these include human lymphoid cells, fibroblasts, human embryonic intestinal epithelial cells, a human colon carcinoma cell line, and human keratinocytes, among others. In response to Cdt, most of these cells exhibit G2 arrest, cellular distension and eventually cell death. However, the effects of Cdt on lymphocytes are different; Cdt-treated lymphocytes do not exhibit cellular distension and are nearly five orders of magnitude more sensitive to Cdt (10-50 pg/ml) relative to most other cells (1-5 μg/ml).

There is compelling evidence that CdtB must be internalized to induce cell cycle arrest. Several investigators have also suggested that CdtB functions as a DNase-like moiety whereby it cleaves DNA and activates the G2 cell cycle checkpoint. This mechanism of action, however, does not account for the huge difference in lymphocyte sensitivity to the toxin. It has been shown that Cdt-treated cells exhibit DNA degradation. However, it has also been shown that Cdt-induced DNA fragmentation in lymphocytes is not the result of direct effects of the toxin, but rather the irreversible effects of cell cycle arrest leading to activation of an apoptotic cascade. The bias in the art toward rationalizing CdtB function is mostly based on its homology with DNase. This bias has obscured the fact that its protein fold, and most likely the reaction mechanism, are also shared with many proteins found in a family of functionally unrelated signaling metalloenzymes that includes phosphatidylinositol (PI)-5-phosphatases.

Therefore, there is a clear need for developing strategies of both inhibiting and using the immunotoxin for therapeutic purposes.

SUMMARY OF THE INVENTION

In one embodiment, the present invention provides a method of treating, inhibiting, or suppressing a lymphoproliferative disease in a subject, comprising the step of administering to said subject a composition comprising a CdtB toxin, a Cdt holotoxin, a mutant CdtB toxin or a mutant Cdt holotoxin, thereby arresting lymphocyte cells at the G2 phase.

In another embodiment, the present invention provides a method of treating, inhibiting, or suppressing a hypersensitivity disease in a subject, comprising the step of administering to the subject a composition comprising a CdtB toxin, a Cdt holotoxin, a mutant CdtB toxin or a mutant Cdt holotoxin.

In another embodiment, the present invention provides a method of treating, inhibiting, or suppressing an inflammatory disease in a subject, comprising the step of administering to said subject a composition comprising a CdtB toxin, a Cdt holotoxin, a mutant CdtB toxin or a mutant Cdt holotoxin.

In one embodiment, the present invention provides a method of treating, inhibiting, or suppressing an autoimmune disease in a subject, comprising the step of administering to said subject a composition comprising a CdtB toxin, a Cdt holotoxin, a mutant CdtB toxin or a mutant Cdt holotoxin, thereby arresting lymphocyte cells at the G2 phase.

In another embodiment, the present invention provides a method of treating an infectious disease in a subject, wherein said infectious disease is caused by a bacterial pathogen, comprising contacting said subject with a composition comprising an agent capable of inhibiting the activity of CdtB.

BRIEF DESCRIPTION OF THE DRAWINGS

A specific embodiment of the present invention will be described with reference to the following drawings, wherein.

DETAILED DESCRIPTION OF THE INVENTION

Figure 1:
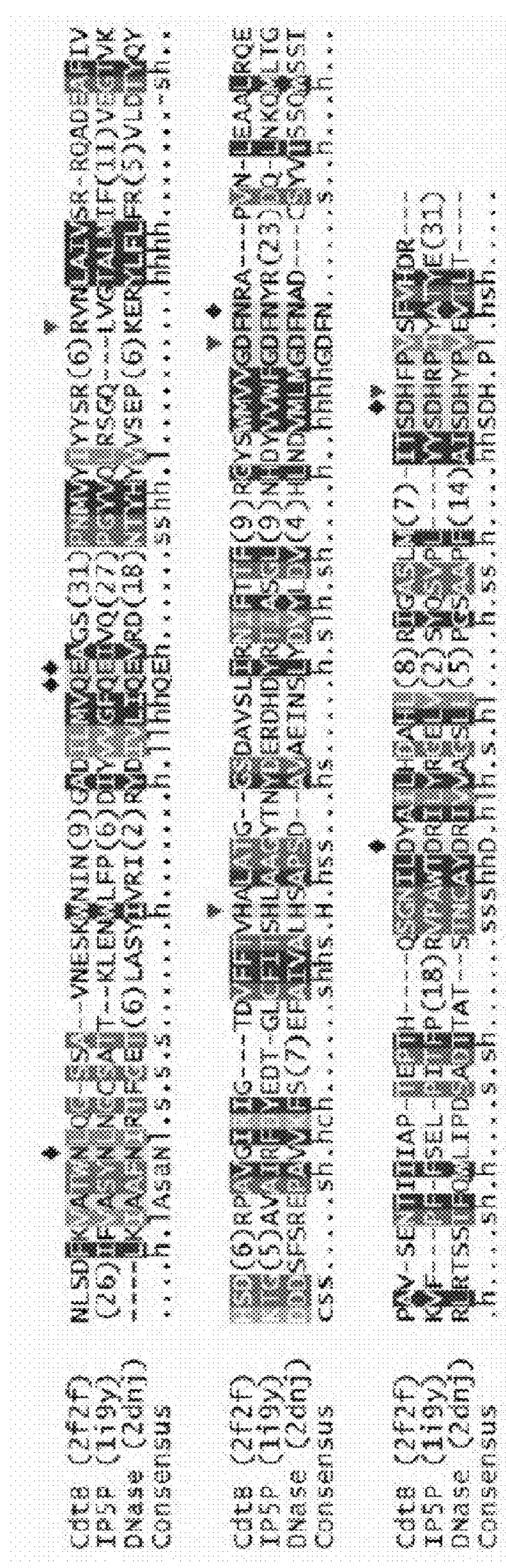
FIG. 1 shows structural alignment. Structural alignment of CdtB (SEQ ID NO: 7), inositol polyphosphate 5-phosphatase (IP5P) (SEQ ID NO: 8) and DNase I (SEQ ID NO: 9) was obtained by MUSTANG and slightly modified after visual inspection of superimposed structures. PDB codes of corresponding structures are shown in parentheses next to protein names. The consensus line (SEQ ID NO: 10) indicates the conservation of small (s), aliphatic (1), hydrophobic (h), charged (c), positive (+) and negative (−) residues, while identical residues are shown as capital letters. Numbers in parentheses within the alignment indicate the residues that were omitted either because of long insertions not shared by all proteins or for the lack of reliable alignment between the three structures. Amino-acid residues mutated in this study are marked by triangles. The remaining residues that are important for catalysis or $Mg^{2+}$ coordination are identified by diamonds.

In one embodiment, provided herein are immunotoxins and their use. In another embodiment, provided herein are compositions comprising Cdt toxins or their inhibitors and their use in another embodiment, in methods for treating infectious and proliferative diseases.

In one embodiment, the term "cytolethal distending toxin" (Cdt) refers to a family of multisubunit toxins produced by a variety of bacteria. In another embodiment, Cdt is a holotoxin composed of three subunits, called CdtA, CdtB, and CdtC, which are encoded by genes arranged in tandem. In one embodiment, the active center of the toxin is in the CdtB subunit having type I deoxyribonuclease-like activity, while in another embodiment, the CdtA and CdtC subunits are involved in the adhesion to target cells. In another embodiment, the holotoxin acts on cells. In one embodiment, the holotoxin acts on epithelial cells. In another embodiment, the holotoxin acts on immune system cells.

In one embodiment, the term "B subunit", as it relates to a specific subunit of the multiunit Cdt, refers to the product of the CdtB gene. In another embodiment, the term "C subunit", as it relates to a specific subunit of the multiunit Cdt, refers to the product of the CdtC gene. In yet another embodiment, the term "A subunit", as it relates to a specific subunit of the multiunit Cdt, refers to the product of the CdtA gene.

In another embodiment, Cdt induces cell cycle arrest at G2/M in a variety of cell types, including, in one embodiment, Chinese Hamster Ovary (CHO), Hela, Hep-2, Vero, CaCo-2, human keratinocyte cell line (HaCat), hamster lung (Don) fibroblast and human T lymphocyte cells. In another embodiment, the cell cycle arrest results in a cessation of cell division. In one embodiment, Cdts produce other effects, including, in another embodiment, progressive cellular distention.

In one embodiment, the B subunit of Cdts possesses DNAse I-like activity and is in another embodiment, structurally similar to DNAse I, which presumably allows the toxin to arrest the cell cycle. In one embodiment, the Cdt holotoxin comprises, Cdt A, B, and C and is, in another embodiment, structurally similar to DNAse I. In one embodiment, the Cdt holotoxin has equal structural homology with inositol polyphosphate 5-phosphatase. In another embodiment, the B subunit has endonuclease activity that results in double strand breaks and blunt ends.

In one embodiment, the compositions and methods of the present invention may use a CdtA subunit, a CdtB subunit, a CdtC subunit, a combination thereof, or a CdtABC holotoxin for example, in a method of treating, inhibiting, or suppressing a lymphoproliferative disorder. In another embodiment, anti-Cdt antibodies for use in the compositions and methods of the present invention may target a CdtA subunit, a CdtB subunit, or a CdtC subunit.

In one embodiment, the amino acid sequence of a CdtA subunit for use in the compositions and methods of the present invention is: LLSSS KNGQVSPSEPSN-FMTLMGQNGALLTVWALAKRNWLWAYP-NIYSQDFGNIRN WKIEPGKHREYFRFVNQS-LGTCIEAYGNGLIHDTCSLDKLAQEFELLPTDSGAV-VIKS VSQGRCVTYNPVSPTYYSTVTLSTCD-GATEPLRDQTWYLAPPVLEATAV (SEQ ID NO: 1). In another embodiment, the CdtA subunit is a homologue of SEQ ID NO: 1. In another embodiment, the CdtA subunit is a variant of SEQ ID NO: 1. In another embodiment, the CdtA subunit is an isoform of SEQ ID NO: 1. In another embodiment, the CdtA subunit is a fragment of SEQ ID NO: 1. Each possibility represents a separate embodiment of the present invention.

In another embodiment, the CdtA subunit has an amino acid sequence set forth in one of the following GenBank entries: AAF81760; AAF19157; AAD10621; AAB06707; AAA18785; NP_860977; AAP78043; YP_002343541; CAL34252; Q46668; AAT92047; AAC70897; AAZ16246; ABV51672.1; YP_001272540.1; BAF63360.1; YP_999805.1; ZP_02270538.1; AAB06707.1; EAQ71960.1; ABJ00842.1; YP_178099.1; AAW34670.1; NP_873397.1; or AAP95786.1. In another embodiment, the CdtA subunit has any CdtA subunit amino acid sequence known in the art. In another embodiment, the CdtA subunit is a homologue of a sequence from one of the above GenBank entries. In another embodiment, the CdtA subunit is a variant of a sequence from one of the above GenBank entries. In another embodiment, the CdtA subunit is an isoform of a sequence from one of the above GenBank entries. In another embodiment, the CdtA subunit is a fragment of a sequence from one of the above GenBank entries. Each possibility represents a separate embodiment of the present invention.

In one embodiment, the nucleotide sequence of a CdtA subunit of the present invention is: ttgctctcttcatccaagaatgga-caggtatcgccgtctgaaccat-caaactttatgactttgatgggacaaaatggggcactgttgactg tctgggcgctagcaaaacgcaattggt-tatgggcttatcccaatatatattcg-caggactttggaaatattcgtaattggaagatagaacc tggtaaacaccgtg-aatattttcgttttgttaatcaatctttaggtacatgtattgaagcttacggtaatggttt-aattcatgatacttgtagtctg gacaaattagcacaagagtttgagttat-tacctactgatagtggtgcggttgtcat-taaaagtgtgtcacaaggacgttgtgtcacttataa tcctgtaagtccaacatattat-tcaacagttacattatcaacttgtgatggcgcaacagaaccattacgtgatcaaaca-tggtatctcgctc ctcctgtattagaagcaacagcggtt (SEQ ID NO: 2). In another embodiment, the nucleotide sequence of the CdtA subunit is a homologue of SEQ ID NO: 2. In another embodiment, the nucleotide sequence of the CdtA subunit is a variant of SEQ ID NO: 2. In another embodiment, the nucleotide sequence of the CdtA subunit is an isoform of SEQ ID NO: 2. In another embodiment, the nucleotide sequence of the CdtA subunit is a fragment of SEQ ID NO: 2. Each possibility represents a separate embodiment of the present invention.

In another embodiment, the CdtA subunit has a nucleic acid sequence set forth in one of the following GenBank entries: AL111168.1; AE017125.1; CP000814.1; AB285204.1; NZ_AASL01000001.1; U51121.1; CP000538.1; CP000468.1; CP000025.1; or AE017143.1. In another embodiment, the CdtA subunit has any CdtA subunit nucleic acid sequence known in the art. In another embodiment, the CdtA subunit is a homologue of a sequence from one of the above GenBank entries. In another embodiment, the CdtA subunit is a variant of a sequence from one of the above GenBank entries. In another embodiment, the CdtA subunit is an isoform of a sequence from one of the above GenBank entries. In another embodiment, the CdtA subunit is a fragment of a sequence from one of the above GenBank entries. Each possibility represents a separate embodiment of the present invention.

In one embodiment, CdtA binds to a specific cell receptor, while in another embodiment, CdtA stabilizes the holotoxin. In one embodiment, analysis of the crystal structure of the toxin suggest that CdtA contains ricin-like domains, leading investigators to propose that it associates with carbohydrate.

In one embodiment, the amino acid sequence of a CdtB subunit of the present invention is: NLSDFKVATWN-LQGSSAVNESKWNINVRQLLSGEQGA-DILMVQEAGSLPSSAVRTS RVIQHGGTPIEEYTWN-LGTRSRPNMVYIYYSRLDVGANRVNLAIVSRRQAD-EAFIVH SDSSVLQSRPAVGIRIGTDVFFTVHA-LATGGSDAVSLIRNIFTTFTSSPSSPERRGYSW MVVGDFNRAPVNLEAALRQEPAVSEN-TIIIAPTEPTHRSGNILDYAILHDAHLPRREQ ARERI-GASLMLNQLRSQITSDHFPVSFVRDR (SEQ ID NO: 3). In another embodiment, the CdtB subunit is a homologue of SEQ ID NO: 3. In another embodiment, the CdtB subunit is a variant of SEQ ID NO: 3. In another embodiment, the CdtB subunit is an isoform of SEQ ID NO: 3. In another embodiment, the CdtB subunit is a fragment of SEQ ID NO: 3. Each possibility represents a separate embodiment of the present invention.

In another embodiment, the CdtB subunit has an amino acid sequence set forth in one of the following GenBank entries: ZP_01072217; NP 860978; YP_002343540; YP_002308521; ZP_03223221; NP_873398; YP_001481648; YP_852557; YP_999804; YP_434821; YP_178098; YP_001272541; ZP_01100899; ZP_01067880; ZP_00370497; or ZP_00369375. In another embodiment, the CdtB subunit has any CdtB subunit amino acid sequence known in the art. In another embodiment, the CdtB subunit is a homologue of a sequence from one of the above GenBank entries. In another embodiment, the CdtB subunit is a variant of a sequence from one of the above GenBank entries. In another embodiment, the CdtB subunit is an isoform of a sequence from one of the above GenBank entries. In another embodiment, the CdtB subunit is a fragment of a sequence from one of the above GenBank entries. Each possibility represents a separate embodiment of the present invention.

In one embodiment, the nucleotide sequence of a CdtB subunit of the present invention is: aacttgagtgatttcaaagtagcaacttggaatctgcaaggttcttcagctgtaaatgaaagtaaatggaatattaatgtgcgccaattatt atcgggagaacaaggtgcagatattttgatggtacaagaagcgggttcattaccaagttcggcagtaagaacctcacgagtaattcaac atgggggaacgccaattgaggaatatacctggaatttaggtactcgctcccgtccaaatatggtctatatttattattcccgtttagatgttg gggcaaaccgagtgaacttagctatcgtgtcacgtcgtcaagccgatgaagcttttatcgtacattctgattcttctgtgcttcaatctcgc ccggcagtaggtatccgcattggtactgatgtatttttacagtgcatgctttggccacaggtggttctgatgcggtaagtttaattcgtaat atcttcactacttttacctcatcaccatcatcaccggaaagacgaggatatagctggatggttgttggtgatttcaatcgtgcgccggttaa tctggaagctgcattaagacaggaacccgccgtgagtgaaaatacaattattattgcgccaacagaaccgactcatcggtccggtaata ttttagattatgcgattttacatgacgcacatttaccacgtcgagagcaagcacgtgaacgtatcggcgcaagtttaatgttaaatcagtta cgctcacaaattacatccgatcattttcctgttagttttgttcgtgatc (SEQ ID NO: 4). In another embodiment, the nucleotide sequence of the CdtB subunit is a homologue of SEQ ID NO: 4. In another embodiment, the nucleotide sequence of the CdtB subunit is a variant of SEQ ID NO: 4. In another embodiment, the nucleotide sequence of the CdtB subunit is an isoform of SEQ ID NO: 4. In another embodiment, the nucleotide sequence of the CdtB subunit is a fragment of SEQ ID NO: 4. Each possibility represents a separate embodiment of the present invention.

In another embodiment, the CdtB subunit has a nucleic acid sequence set forth in one of the following GenBank entries: AL111168.1; AL627271.1; AE017125.1; CP000814.1; AB285204.1; EU794049.1; DQ092613.1; CP000468.1; CP000026.1; CP000155.1; CP000025.1; AE017143.1; CP000538.1; U51121.1; NZ_AASL01000001.1; or AE014613.1. In another embodiment, the CdtB subunit has any CdtB subunit nucleic acid sequence known in the art. In another embodiment, the CdtB subunit is a homologue of a sequence from one of the above GenBank entries. In another embodiment, the CdtB subunit is a variant of a sequence from one of the above GenBank entries. In another embodiment, the CdtB subunit is an isoform of a sequence from one of the above GenBank entries. In another embodiment, the CdtB subunit is a fragment of a sequence from one of the above GenBank entries. Each possibility represents a separate embodiment of the present invention.

In one embodiment, the amino acid sequence of a CdtC subunit of the present invention is: ESNPDPTTYPDVELSPPPRISLRSLLTAQPIKNDHYDSHNYLSTHWELIDYKGKEYEK LRDGGTLVQFKVVGAAKCFAFPGEGTTDCKDIDHTVFNLIPTNTGAFLIKDALLGFC MTSHDFDDLRLEPCGISVSGRTFSLAYQWGILPPFGPSKILRPPVGRNQGS (SEQ ID NO: 5). In another embodiment, the CdtC subunit is a homologue of SEQ ID NO: 5. In another embodiment, the CdtC subunit is a variant of SEQ ID NO: 5. In another embodiment, the CdtC subunit is an isoform of SEQ ID NO: 5. In another embodiment, the CdtC subunit is a fragment of SEQ ID NO: 5. Each possibility represents a separate embodiment of the present invention.

In another embodiment, the CdtC subunit has an amino acid sequence set forth in one of the following GenBank entries: YP_002343539.1; NP_860979.1; YP_001481647.1; YP_001272542.1; YP_852558.1; YP_999803.1; YP_178097.1; NP_873399.1; CAL34250.1; AAP78045.1; ABV51670.1; BAF63362.1; ABJ00844.1; EAQ72030.1; AAB06709.1; ZP_02270536.1; or AAW34668.1. In another embodiment, the CdtC subunit has any CdtC subunit amino acid sequence known in the art. In another embodiment, the CdtC subunit is a homologue of a sequence from one of the above GenBank entries. In another embodiment, the CdtC subunit is a variant of a sequence from one of the above GenBank entries. In another embodiment, the CdtC subunit is an isoform of a sequence from one of the above GenBank entries. In another embodiment, the CdtC subunit is a fragment of a sequence from one of the above GenBank entries. Each possibility represents a separate embodiment of the present invention.

In one embodiment, the nucleotide sequence of a CdtC subunit of the present invention is: gaatcaaatcctgatccgactacttatcctgatgtagagttatcgcctcctccacgtattagcttgcgtagtttgcttacggctcaaccaatt aaaaatgaccattatgattcacataattatttaagtacacattgggaattaattgattacaagggaaaagaatatgaaaaattacgtgacgg tggtacgttggttcaatttaaagtggtcggtgcagcaaaatgttttgctttcccaggcgaaggcacaactgattgtaaagatattgatcata ctgtgtttaaccttattccaactaatacaggtgcgtttttaatcaaagatgcctattaggattttgtatgacaagccatgactttgatgatttg aggcttgaaccttgtggaatttcagtgagtggtcgaaccttttcgttggcgtatcaatggggaatattacctccttttgggccaagtaaaatt ttaagaccaccggtggggagaaatcagggtagc (SEQ ID NO: 6). In another embodiment, the nucleotide sequence of the CdtC subunit is a homologue of SEQ ID NO: 6. In another embodiment, the nucleotide sequence of the CdtC subunit is a variant of SEQ ID NO: 6. In another embodiment, the nucleotide sequence of the CdtC subunit is an isoform of SEQ ID NO: 6. In another embodiment, the nucleotide sequence of the CdtC subunit is a fragment of SEQ ID NO: 6. Each possibility represents a separate embodiment of the present invention.

In another embodiment, the CdtC subunit has a nucleic acid sequence set forth in one of the following GenBank entries: AL111168.1; AE017125.1; CP000814.1; AB285204.1; CP000468.1; CP000538.1; U51121.1; NZ_AASL01000001.1; or CP000025.1.

In another embodiment, the CdtC subunit has any CdtC subunit nucleic acid sequence known in the art. In another embodiment, the CdtC subunit is a homologue of a sequence from one of the above GenBank entries. In another embodiment, the CdtC subunit is a variant of a sequence from one of the above GenBank entries. In another embodiment, the CdtC subunit is an isoform of a sequence from one of the above GenBank entries. In another embodiment, the CdtC subunit is a fragment of a sequence from one of the above GenBank entries. Each possibility represents a separate embodiment of the present invention.

In one embodiment, CdtC comprises a cholesterol recognition site and, in one embodiment, CdtC binds to both cell and model membranes in a cholesterol dependent manner.

In one embodiment, the PI-3,4,5-triphosphate (PI-3,4,5-P3) phosphatase activity of CdtB is similar to that of the tumor suppressor phosphatase, PTEN (phosphatase and tensin homolog deleted on chromosome ten), and, in another embodiment, to the tumor suppressor phosphatase, src homology 2-containing inositol phosphatase (SHIP). In another embodiment, Cdt toxicity correlates with phosphatase activity; and in one embodiment, lymphocytes treated with toxin exhibit reduced PI-3,4,5-P3 levels. In another embodiment, lymphocyte sensitivity to Cdt-induced G2 arrest, correlates with intracellular levels of PI-3,4,5-P3.

In one embodiment, lipids and PI-3,4,5-P3 in particular, have a central role in regulating an array of biological responses which include cell growth, proliferation, and survival. PI-3,4,5-P3 is normally maintained at low levels and increases rapidly in response to a variety of signals that involve plasma membrane recruitment and activation of PI3K. In one embodiment, normal cell function requires that PI-3,4,5-P3 levels be tightly regulated. In one embodiment, three enzymes, PTEN, SHIP1, and SHIP2, play a role in regulating PI-3,4,5-P3 levels. In one embodiment, PTEN is a good lipid phosphatase whose substrates are 3-phosphatidylinositol phosphates and, in one embodiment, hydrolyze PI-3,4,5-P3 to PI-4,5-P2. In one embodiment, SHIP1 and SHIP2 are inositol 5-phosphatases. In one embodiment, SHIP2 is ubiquitously expressed. In one embodiment, SHIP1 is found in a limited subset of cells, which in one embodiment, includes most immune cells. Both SHIP enzymes hydrolyze PI-3,4,5-P3 to PI-3,4-P2 and inositol 1,3,4,5-tetrakisphosphate to inositol 1,3,4 triphosphate. In another embodiment, the active Cdt subunit, CdtB, is capable of hydrolyzing PI-3,4,5-P3 and functions in one embodiment, as an inositol 5-polyphosphate phosphatase, similar to the SHIP enzymes. In another embodiment, and unlike the SHIPs, CdtB does not hydrolyze inositol 1,3,4,5-tetrakisphosphate.

In one embodiment, elevated levels of PI-3,4,5-P3 are critical for the survival of Jurkat and many other leukemic cell lines. In another embodiment, Jurkat cells were the most sensitive to Cdt-induced G2 arrest; consistent with their dependence on elevated levels of PI-3,4,5-P3 for survival. In yet another embodiment, HUT78 cells, a cutaneous T cell lymphoma cell line that contains functional levels of both PTEN and SHIP1 and concomitant lower intracellular levels of PI-3,4,5-P3, are resistant to the effects of Cdt at certain concentrations. In one embodiment, CEM and Molt cells, which contain normal SHIP1 expression and activity, but lack PTEN, were responsive to Cdt.

In one embodiment, the invention provides a method of treating a lymphoproliferative disease in a subject, comprising the step of administering to the subject a composition comprising an isolated CdtB, CdtA, CdtC toxin or its respective mutants, thereby arresting lymphocyte cells at the G2 phase. In another embodiment, the invention provides a method of treating a lymphoproliferative disease in a subject, comprising the step of administering to the subject a composition comprising an isolated holotoxin, further comprising CdtABC, or its mutant, thereby arresting lymphocyte cells at the G2 phase.

In one embodiment, the CdtB mutant used in the methods described herein for cells at the G2 phase, is a substitution mutant, or a fusion protein or a combination thereof in other discrete embodiments. In one embodiment, the CdtB mutant is $CdtB^{H274Q}$. In another embodiment, the CdtB mutant is $CdtB^{A163N}$. In another embodiment, the CdtB mutant is $CdtB^{A163Q}$.

In one embodiment, methods for constructing the CdtB mutants used in the compositions and methods of the present invention are conducted as described herein, and in particular as described in the materials and methods in the Examples section below.

In one embodiment, mutation of the CdtB gene at loci that are believed to be critical to DNase activity resulted in a decline in PI-3,4,5-P3 phosphatase activity. In one embodiment, mutation of the CdtB gene at loci described herein resulted in a decline in PI-3,4,5-P3 phosphatase activity, and, in another embodiment, in a loss of toxicity, which in one embodiment, is G2 cell cycle arrest. Thus, in one embodiment, In another embodiment, CdtB has dual functions whereby DNase activity is important for toxicity in some cell types while lipid phosphatase activity is critical for toxicity in other cells such as lymphocytes, in one embodiment.

In one embodiment, elevated levels of PI-3,4,5-P3 are critical for the survival of Jurkat and many other leukemic cell lines. In one embodiment, Jurkat cells are the most sensitive to Cdt-induced G2 arrest; consistent with their dependence on elevated levels of PI-3,4,5-P3 for survival.

In one embodiment, PI-3,4,5-P3 levels are elevated in certain forms of cancer, as is known in the art. In one embodiment, Cdt or the CdtB subunit may be used to treat such forms of cancer. In one embodiment, Cdt has a high affinity for lymphocytes. In one embodiment, CdtB may be targeted to tumors using targeting molecules that are known in the art, which in one embodiment, are antibodies specific for tumor-specific antigens.

In one embodiment, methods of the present invention treat, inhibit, suppress, or ameliorate symptoms related to a disease, disorder, and/or condition described herein by lowering PI-3,4,5-P3 levels in a target cell.

In one embodiment, the active Cdt subunit, CdtB, is capable of functioning as a PI-3,4,5-P3 phosphatase and this activity appears to be critical, in another embodiment, to toxin-induced G2 arrest in lymphocytes. In one embodiment, the in vitro phosphatase activity of CdtB is much more robust than its nuclease activity, at least in relative terms when compared with other similar enzymes, and in another embodiment, mutations such as the $CdtB^{R117A}$ mutation, either alone or in the context of the triple DNA-binding mutant, eradicates the G2 arrest normally induced by $CdtB^{WT}$ without significantly affecting the DNase activity, support the candidacy of PI-3,4,5-P3 as the major cellular target of CdtB. In one embodiment, the $CdtB^{R117A}$ mutation severely affects the PI-3,4,5-P3 phosphatase activity of CdtB. Two arginine residues in the active site of inositol phosphate 5-phosphatases interact with either phosphate or hydroxyl groups of inositol and a similar function of R117 could explain the failure of kinetic measurements to detect any product with the CdtBR117A mutant. In another embodiment, the mutation of the flanking valine, V118E, also eliminates the G2 arrest normally induced by CdtBWT, even though this particular mutation is expected to boost the DNase activity of CdtB. In one embodiment, the ability of CdtB and its mutants to cause cell cycle arrest always correlates with their phosphatase activities and only sometimes with their DNase activities.

Thus, in one embodiment, mutants for use in the present invention maintain their phosphatase activity, maintaining their ability to arrest cell cycle in a target cell, which in one embodiment, is a lymphocyte. In another embodiment, mutants for use in the present invention retain their DNase activity, while in another embodiment, mutants for use in the present invention do not retain their DNase activity. Each of these possibilities represents a separate embodiment.

In one embodiment, DNase activity is important for Cdt toxicity in some cell types, while in another embodiment, phosphatase activity is important for Cdt toxicity in some cell types, which in one embodiment, are lymphocytes.

In one embodiment, mutants of the present invention have increased DNase activity. In one embodiment, mutants of the present invention induce apoptosis. In one embodiment, mutants of the present invention exhibit reduced phosphatase activity and toxicity (G2 arrest). In one embodiment, mutants of the present invention exhibit reduced phosphatase activity and toxicity (G2 arrest), increased DNase activity, and induction of apoptosis in the host cell. Thus, in one embodiment, mutants of the present invention may be used to treat forms of cancer that do not involve PIP3 alterations, as are known in the art.

In another embodiment, the invention provides a method of inhibiting or suppressing a lymphoproliferative disease in a subject, comprising the step of administering to the subject a composition comprising an isolated CdtB, CdtA, CdtC toxin or its respective mutants, thereby arresting lymphocyte cells at the G2 phase. In another embodiment, the invention provides a method of inhibiting or suppressing a lymphoproliferative disease in a subject, comprising the step of administering to the subject a composition comprising an isolated holotoxin, further comprising CdtABC, or its mutant, thereby arresting lymphocyte cells at the G2 phase.

In one embodiment, provided herein is a method of ameliorating symptoms associated with a lymphoproliferative disease in a subject, comprising the step of administering to the subject a composition comprising an isolated CdtB, CdtA, CdtC toxin or its respective mutants, thereby arresting lymphocyte cells at the G2 phase. In another embodiment, provided herein is a method of ameliorating symptoms associated with a lymphoproliferative disease in a subject, comprising the step of administering to the subject a composition comprising an isolated holotoxin, further comprising CdtABC, or its mutant, thereby arresting lymphocyte cells at the G2 phase.

In another embodiment, the invention provides a composition for treating a lymphoproliferative disease in a subject, comprising an isolated mutant CdtB toxin, an isolated mutant CdtA toxin, an isolated mutant CdtC toxin, thereby arresting lymphocyte cells at the G2 phase. In another embodiment, the invention provides a composition for treating a lymphoproliferative disease in a subject comprising an isolated CdtABC holotoxin mutant, thereby arresting lymphocyte cells at the G2 phase.

In one embodiment, provided herein is a method of treating a lymphoproliferative disease, or inhibiting or suppressing a lymphoproliferative disease in another embodiment, or in another embodiment, ameliorating symptoms associated with a lymphoproliferative disease in a subject, comprising the step of administering to the subject a composition comprising an isolated CdtB toxin or its mutant, thereby arresting lymphocyte cells at the G2 phase, and treating the lymphoproliferative disease.

In one embodiment, lymphoproliferative disorders are a set of disorders characterized by the abnormal proliferation of lymphocytes into a monoclonal lymphocytosis. In one embodiment, the two major types of lymphocytes are B cells and T cells, which are derived from pleuripotent hematopoetic stem cells in the bone marrow. Individuals who have some sort of immunodysfunction are susceptible to developing a lymphoproliferative disorder because when any of the numerous control points of the immune system become dysfunctional, immunodeficiency or deregulation of lymphocytes is more likely to occur. In one embodiment, lymphoproliferative disorders are associated with inherited genetic mutations, while in another embodiment, they are associated with environmental factors and/or iatrogenic causes.

In one embodiment, a lymphoproliferative disorder that may be treated, inhibited, or suppressed using the compositions and methods of the present invention is chronic lymphocytic leukemia; acute lymphoblastic leukemia; hairy cell leukemia; lymphomas; multiple myeloma; Waldenstrom's macroglobulinemia; Wiskott-Aldrich syndrome; post-transplant lymphoproliferative disorder; Autoimmune lymphoproliferative syndrome (ALPS); or Lymphoid interstitial pneumonia. In another embodiment, a lymphoproliferative disorder that may be treated, inhibited, or suppressed using the compositions and methods of the present invention is an X-linked Lymphoproliferative disorder, which in one embodiment, is characterized by a mutation on the X chromosome that has been found to be associated with a T and NK cell lymphoproliferative disorder. In another embodiment, a lymphoproliferative disorder that may be treated, inhibited, or suppressed using the compositions and methods of the present invention is an autosomal lymphoproliferative disorder. In another embodiment, a lymphoproliferative disorder that may be treated, inhibited, or suppressed using the compositions and methods of the present invention is caused by a viral infection, which in one embodiment, is a congenital HIV infection. In another embodiment, a lymphoproliferative disorder that may be treated, inhibited, or suppressed using the compositions and methods of the present invention is due to Iatrogenic causes, which in one embodiment, are associated with organ transplantation and immunosuppressant therapies. In most reported cases, these cause B cell lymphoproliferative disorders, however some T cell variations have been described. The T cell variations are usually caused by the prolonged use of T cell suppressant drugs, such as sirolimus, tacrolimus or cyclosporine A.

In one embodiment, the lymphoproliferative disease to be treated is chronic Beryllium disease (CBD), or in other embodiments Hodgkin's disease (HD), non-Hodgkin's Lymphoma, HIV-induced lymphoproliferation, or severe periodontic lymphoproliferation-induced inflammation.

In one embodiment, provided herein is a method of treating a hypersensitivity disease in a subject, comprising the step of administering to the subject a composition comprising an isolated CdtB toxin or its mutant. In another embodiment, provided herein is a method of treating a hypersensitivity disease in a subject, comprising the step of administering to the subject a composition comprising an isolated holotoxin, further comprising CdtABC, or its mutant.

In another embodiment, provided herein is a method of inhibiting or suppressing a hypersensitivity disease in a subject, comprising the step of administering to the subject a composition comprising an isolated CdtB toxin or its mutant. In another embodiment, the invention provides a method of inhibiting or suppressing a hypersensitivity disease in a subject, comprising the step of administering to the subject a composition comprising an isolated holotoxin, further comprising CdtABC, or its mutant.

In another embodiment, the invention provides a method of eliminating symptoms associated with a hypersensitivity disease in a subject, comprising the step of administering to the subject a composition comprising an isolated CdtB toxin or its mutant. In another embodiment, the invention provides a method of eliminating symptoms associated with a hypersensitivity disease in a subject, comprising the step of administering to the subject a composition comprising an isolated holotoxin, further comprising CdtABC, or its mutant.

In another embodiment, the invention provides a composition for treating a hypersensitivity disease in a subject, comprising an isolated CdtB toxin mutant. In another embodiment, the invention provides a composition for treating a hypersensitivity disease in a subject comprising an isolated CdtABC holotoxin mutant.

In one embodiment, a hypersensitivity disease is a delayed hypersensitivity (DH), or in another embodiment, delayed-type hypersensitivity (DTH) disease, which in one embodiment, takes 24 to 72 hours to develop and is mediated by T lymphocytes rather than by antibodies. In one embodiment, it is a subset of type IV hypersensitivity involving cytokine release and macrophage activation, as opposed to direct cytolysis. In one embodiment, the delayed type hypersensitivity reactions are probably important for host defense against intracellular parasites such as tuberculosis and certain viruses and are prevalent in certain disease such as sarcoidosis, Wegener's granulomatosis, and polymyositis. In some diseases, such as chronic granulomatous disease of childhood, granuloma formation can lead to obstruction of vital structures such as the esophagus or ureters. The contact dermatitis is caused by sensitization to certain simple chemicals.

In one embodiment, the compositions and methods of the present invention treat DTH disease, which in one embodiment is epidermal (in one embodiment, contact dermatitis, reaction to organic chemicals, poison ivy, heavy metals), in another embodiment, is intradermal (in one embodiment, reaction to tuberculin, lepromin). In one embodiment, DTH disease is contact dermatitis, chronic transplant rejection, multiple sclerosis.

In one embodiment, delayed hypersensitivity reaction is contact hypersensitivity or tuberculin-type hypersensitivity, while in another embodiment, it is a granulomatous reaction, where in one embodiment, granulomas are formed by the aggregation and proliferation of macrophages, and may persist for weeks.

In one embodiment, Type IV or delayed type hypersensitivity (DTH), is most seriously manifested when antigens (for example those of tubercle bacilli) are trapped in a macrophage and cannot be cleared. In one embodiment, T cells are then stimulated to elaborate lymphokines which mediate a range of inflammatory responses. In another embodiment, graft rejection and allergic contact dermatitis are types of DTH.

In one embodiment, the invention provides a method of treating an inflammatory disorder in a subject, comprising the step of administering to the subject a composition comprising an isolated CdtB toxin or its mutant. In another embodiment, the invention provides a method of treating an inflammatory disorder in a subject, comprising the step of administering to the subject a composition comprising an isolated holotoxin, further comprising CdtABC, or its mutant.

In another embodiment, the invention provides a method of inhibiting or suppressing an inflammatory disease in a subject, comprising the step of administering to the subject a composition comprising an isolated holotoxin, further comprising CdtABC, or its mutant. In another embodiment, the invention provides a method of inhibiting or suppressing an inflammatory disease in a subject, comprising the step of administering to the subject a composition comprising an isolated CdtB toxin or its mutant.

In another embodiment, the invention provides a method of eliminating symptoms associated with an inflammatory disease in a subject, comprising the step of administering to the subject a composition comprising an isolated CdtB toxin or its mutant. In another embodiment, the invention provides a method of eliminating symptoms associated with an inflammatory disease in a subject, comprising the step of administering to the subject a composition comprising an isolated holotoxin, further comprising CdtABC, or its mutant.

In another embodiment, the invention provides a composition for eliminating symptoms associated with an inflammatory disease in a subject, comprising an isolated mutant CdtB toxin. In another embodiment, the invention provides a composition for eliminating symptoms associated with an inflammatory disease in a subject, comprising an isolated mutant CdtABC holotoxin.

In one embodiment, an inflammatory disease is rheumatoid arthritis, osteoarthritis inflammatory lung disease, inflammatory bowel disease, which in one embodiment is ulcerative colitis or Crohn's Disease, atherosclerosis or psoriasis.

In one embodiment, compositions of the present invention may be used to treat, inhibit, or suppress autoimmune disease. In one embodiment, an autoimmune disease is Dermatomyositis; Diabetes mellitus type 1; Endometriosis; Goodpasture's syndrome; Grave's disease; Guillain-Barré syndrome (GBS); Hashimoto's thyroiditis; Hidradenitis suppurativa; Idiopathic thrombocytopenic purpura; Interstitial cystitis; Lupus erythematosus; Mixed Connective Tissue Disease; Morphea; Multiple sclerosis (MS); Myasthenia gravis; Narcolepsy; Neuromyotonia; Pemphigus Vulgaris; Pernicious anaemia; Polymyositis; Primary biliary cirrhosis; Reactive arthritis; Rheumatoid arthritis; Schizophrenia; Scleroderma; Sjøgren's syndrome; Systemic lupus erythematosus; Temporal arteritis (also known as "giant cell arteritis"); Ulcerative Colitis (one of two types of idiopathic inflammatory bowel disease "IBD"); Vasculitis; Vitiligo; or Wegener's granulomatosis.

In one embodiment, a composition for use in the methods of the present invention further comprises PI-(3,4,5)-$P_3$. In another embodiment, a composition for use in the methods of the present invention, in one embodiment, for methods for treating lymphoproliferative disorders, hypersensitivity disorders, or inflammatory diseases, further comprises an agent that increases cellular levels of PI-(3,4,5)-$P_3$. Such agents are known in the art and include inter alia, phosphatase inhibitors such as PTEN, SHIP1, and SHIP2 and, in another embodiment, PI-3 kinases.

In one embodiment, a composition for use in the methods of the present invention comprises a mutant CdtB toxin or Cdt holotoxin, which in one embodiment, is a fusion protein.

In one embodiment, the invention provides a composition for treating a Cdt toxin poisoning in a subject, comprising an agent capable of inhibiting the activity of CdtB, wherein the agent is an anti-CdtB antibody or its functional fragment, a phosphatase inhibitor or a combination thereof.

In another embodiment, the present invention provides a method of treating a Cdt toxin poisoning in a subject, comprising the step of administering to said subject a composition comprising an agent capable of inhibiting the activity of CdtB, wherein the agent is an anti-CdtB antibody or its functional fragment, a phosphatase inhibitor or a combination thereof. In another embodiment, the present invention provides a method of inhibiting or suppressing a Cdt toxin poisoning in a subject, comprising the step of administering to said subject a composition comprising an agent capable of inhibiting the activity of CdtB, wherein the agent is an anti-CdtB antibody or its functional fragment, a phosphatase inhibitor or a combination thereof. In another embodiment, the present invention provides a method of ameliorating symptoms associated with a Cdt toxin poisoning in a subject, comprising the step of administering to said subject a composition comprising an agent capable of inhibiting the activity of CdtB, wherein the agent is an anti-CdtB antibody or its functional fragment, a phosphatase inhibitor or a combination thereof.

In one embodiment, the Cdt toxin poisoning is mediated by CdtA, CdtB, CdtC, or a combination thereof.

In another embodiment, the invention provides a method of preventing binding of CdtABC to a cell surface receptor, comprising the step of administering an anti-CdtA antibody, anti-CdtB antibody, anti-CdtC antibody, or a functional fragment of an anti-CdtA antibody, anti-CdtB antibody, or anti-CdtC antibody, or a combination thereof.

In one embodiment, the invention provides a method of treating an infectious disease in a subject, wherein the infectious disease is caused by a bacterial pathogen, comprising the step of administering to the subject a composition comprising an agent capable of inhibiting the activity of CdtB.

In another embodiment, the invention provides a method of suppressing or inhibiting an infectious disease in a subject, wherein the infectious disease is caused by a bacterial pathogen, comprising the step of administering to the subject a composition comprising an agent capable of inhibiting the activity of CdtB.

In another embodiment, the invention provides a method of ameliorating symptoms associated with an infectious disease in a subject, wherein the infectious disease is caused by a bacterial pathogen, comprising the step of administering to the subject a composition comprising an agent capable of inhibiting the activity of CdtB.

In another embodiment, the invention provides a composition for ameliorating symptoms associated with an infectious disease in a subject, wherein the infectious disease is caused by a bacterial pathogen, comprising an agent capable of inhibiting the activity of CdtB.

In one embodiment, an agent capable of inhibiting the activity of CdtB is an anti-CdtB antibody. In another embodiment, an agent capable of inhibiting the activity of CdtB is a functional fragment of an anti-CdtB antibody. In another embodiment, an agent capable of inhibiting the activity of CdtB is a PI-3 kinase inhibitor. In another embodiment, an agent capable of inhibiting the activity of CdtB is an inositol polyphosphate 5-phosphatase inhibitor.

In another embodiment, an agent capable of inhibiting the activity of CdtB is a phosphatase inhibitor, which in one embodiment, is tungstate, in another embodiment, orthovanadate in another embodiment, vanadate, in another embodiment, molybdate, in another embodiment, phosphate, or, in another embodiment, a combination thereof. In another embodiment, an agent capable of inhibiting the activity of CdtB is a combination of the agents described herein.

In one embodiment, the inositol polyphosphate 5-phosphatase inhibitor used as the agent in the methods and compositions described herein, is a SHIP2 protein or its fragment, D-myo-inositol-1,3,4,5-tetrakisphosphate, or 2,2-difluoro-2-deoxy-myo-inositol, their pharmaceutically acceptable salt or a combination thereof in other discrete embodiments.

In another embodiment, the methods of the present invention comprise contacting a subject with a composition comprising an agent capable of inhibiting the activity of CdtB as well as an agent capable of reducing the concentration of PI-(3,4,5)-$P_3$, whereby the agent capable of reducing the concentration of PI-(3,4,5)-$P_3$ is PTEN, or MMAC1, TEP1 or a combination thereof in other discrete embodiments.

In one embodiment, the term "antibody" encompasses, but is not limited to, whole immunoglobulin (i.e., an intact antibody) of any class. In another embodiment, native antibodies are usually heterotetrameric glycoproteins, composed of two identical light (L) chains and two identical heavy (H) chains. In one embodiment, each light chain is linked to a heavy chain by one covalent disulfide bond, while the number of disulfide linkages varies between the heavy chains of different immunoglobulin isotypes. In another embodiment, each heavy and light chain also has regularly spaced intrachain disulfide bridges. In yet another embodiment, each heavy chain has at one end a variable domain (V(H)) followed by a number of constant domains. While in another embodiment, each light chain has a variable domain at one end (V(L)) and a constant domain at its other end; the constant domain of the light chain is aligned with the first constant domain of the heavy chain, and the light chain variable domain is aligned with the variable domain of the heavy chain.

In one embodiment, the term "antibody" includes complete antibodies (e.g., bivalent IgG, pentavalent IgM) or fragments of antibodies which contain an antigen binding site in other embodiments. Such fragments include, in one embodiment, Fab, $F(ab')_2$, Fv and single chain Fv (scFv) fragments. In one embodiment, such fragments may or may not include antibody constant domains. In another embodiment, Fab's lack constant domains which are required for Complement fixation. ScFvs are composed of an antibody variable light chain ($V_L$) linked to a variable heavy chain ($V_H$) by a flexible hinge. ScFvs are able to bind antigen and can be rapidly produced in bacteria. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$-$C_{H1}$ and $V_L$-$C_L$) comprise a Fab. Complete antibodies are obtained in one embodiment, from such a library by replacing missing constant domains once a desired $V_H$-$V_L$ combination has been identified.

Antibodies of the invention can be monoclonal antibodies (mAb) in one embodiment, or polyclonal antibodies in another embodiment. Antibodies of the invention which are useful for the compositions, methods and kits of the invention can be from any source, and in addition may be chimeric. In one embodiment, sources of antibodies can be from a mouse, or a rat, a plant, or a human in other embodiments. Antibodies of the invention which are useful for the compositions, and methods of the invention have reduced antigenicity in humans (to reduce or eliminate the risk of formation of anti-human antibodies), and in another embodiment, are not antigenic in humans. Chimeric antibodies for use in the invention contain in one embodiment, human amino acid sequences and include humanized antibodies which are non-human antibodies substituted with sequences of human origin to reduce or eliminate immunogenicity, but which retain the antigen binding characteristics of the non-human antibody. Accordingly, in one embodiment, provided herein is a composition for treating a Cdt toxin poisoning in a subject, comprising an anti-CdtB antibody or its functional fragment.

In one embodiment, there are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. In another embodiment, one skilled in the art would recognize the comparable classes for mouse or other species.

In one embodiment, the terms "immunoglobulin heavy chain or fragments thereof" and "immunoglobulin light chain or fragments thereof" encompass chimeric peptides and hybrid peptides, with dual or multiple antigen or epitope specificities, and fragments, including hybrid fragments. In another embodiment, fragments of the heavy chains and/or fragments of the light chains that retain the ability to bind their specific antigens are provided. In yet another embodiment, fragments of the heavy chains and/or fragments of the light chains that maintain SKCG-1 protein binding activity are included within the meaning of the terms "immunoglobulin heavy chain or fragments thereof" and "immunoglobulin light chain and fragments thereof," respectively. Such heavy chains and light chains and fragments thereof, respectively, can be made in one embodiment, by techniques known in the art and can be screened for specificity and activity according to the methods set forth in the Examples and in general methods for producing antibodies and screening antibodies for specificity and activity.

In one embodiment, tyrosine phosphorylation plays an essential role in the control of lymphocyte function. This control is exerted, in another embodiment, by a network of tyrosine kinases and phosphotyrosine phosphatases. Two different processes that induce B cell apoptosis, have been shown in one embodiment, to act through tyrosine phosphorylation. Another phosphotyrosine phosphatase inhibitor used in the compositions and methods described herein is dephostatin or a PI-3 kinase inhibitor, an inositol polyphosphate 5-phosphatase inhibitor or a combination thereof.

In one embodiment, the PI-3K inhibitor used in the compositions and methods described herein is LY290004, 2-(4-morphonyl)-8-phenyl-4H-1-benzopyran-4-one (LY294002), or Wortmannin or a combination thereof in other discrete embodiment. In another embodiment, the PI-3K inhibitor is ET-18-$OCH_3$, LY 294002, InSolution™ LY 294002, LY 303511, L-α-Phosphatidylinositol-4,5-bisphosphate, Dipalmitoyl-, Pentaammonium Salt, PI 3-Kγ Inhibitor, PI 3-Ka Inhibitor IV, PI 3-Kα Inhibitor VIII, PI 3-Kβ Inhibitor VI, TGX-221, PI 3-Kγ Inhibitor II, PI 3-Kγ/CKII Inhibitor, PI 3-Kγ Inhibitor VII, PI-103, Quercetin, Dihydrate, PI3-K alpha Inhibitor 1 (PI-103), PI3-K alpha Inhibitor 2, PI3-K gamma Inhibitor 1 (AS605240), PI3-K gamma Inhibitor 2 (AS604850), PI3-K Inhibitor (LY294002), Resveratrol, or a combination thereof. Other PI-3-K inhibitors are known in the art and may be used in the compositions and methods of the present invention.

In one embodiment, provided herein is a composition for treating Cdt toxin poisoning in a subject, comprising a phosphatase inhibitor, wherein the phosphatase inhibitor is LY290004. In another embodiment, the compositions described herein, are used in the methods provided. In another embodiment a phosphatase inhibitor for use in the compositions and methods of the present invention is 1,4-Dimethylendothall; Artesunate; Benzylphosphonic Acid; Benzylphosphonic Acid-$(AM)_2$; BML-267; Calcineurin Autoinhibitory Peptide (CN412); Calyculin A; Cantharidic Acid; Cantharidin; CinnGEL; CinnGEL 2Me; Cypermethrin; Deltamethrin; D-p-Bromotetramisole Oxalate; Endothall; Fenvalerate; Gossypol; L-p-Bromotetramisole Oxalate; Microcystin LR; NSC-95397; or a combination thereof. In another embodiment, the phosphatase inhibitor is sodium fluoride, sodium orthovanadate, sodium pyrophosphate or -glycerophosphate. In another embodiment, the phosphatase inhibitor is BN82002 hydrochloride; Calyculin A from Discodermia calyx; Cantharidic acid; Cantharidin; Cypermethrin; Dephostatin; Ethyl-3,4-dephostatin; Fostriecin sodium salt from *Streptomyces pulveraceus*; MA751; Methyl-3,4-dephostatin; Microcystin LR from *Microcystis aeruginosa*; NSC 95397; Norcantharidin; Okadaic acid ammonium salt; Okadaic acid; Okadaic acid potassium salt; Okadaic acid sodium salt; Phenylarsine oxide; Protein Phosphatase Inhibitor-2 from rabbit; or Sodium orthovanadate. Other phosphatase inhibitors are known in the art and may be used in the compositions and methods of the present invention.

In one embodiment, the compositions and methods of the present invention comprise an agent capable of reducing the concentration of PI-(3, 4, 5)-$P_3$ which, in one embodiment, is PTEN. PTEN (known in one embodiment, as MMAC1 or TEP1), is a dual-specificity protein phosphatase that is implicated, in one embodiment, as a phosphoinositide phosphatase in the insulin-signaling pathway. In another embodiment, PTEN dephosphorylates phosphatidylinositol 3,4,5-triphosphate (PIP3), an acidic lipid that is involved in cellular growth signaling. In another embodiment, PTEN affects both cell size and cell cycle progression during eye development in *Drosophila*. Accordingly, in one embodiment, provided herein is a composition for treating a Cdt toxin poisoning in a subject, comprising MMAC1 and an agent capable of inhibiting the activity of CdtB, wherein the agent is an anti-CdtB antibody or its functional fragment, a phosphatase inhibitor or a combination thereof.

In another embodiment, the Cdt toxin poisoning is caused by *Escherichia coli*, or *Campylobacter jejuni, Haemophilus ducreyi, Shigella dysenteriae, Actinobacillus actinomycetemcomitans*, or a combination thereof in other discrete embodiments of the bacteria whose poisoning is sought to be treated. In one embodiment, the compositions described hereinabove, are used in the methods provided herein. In one embodiment, provided herein is a method of treating an infectious disease in a subject, whereby the infectious disease is caused by a bacterial pathogen, comprising contacting the subject with a composition comprising an agent capable of inhibiting the activity of CdtB.

As used herein, the term "hybridization" refers, in one embodiment, to cumulative hydrogen bonding between complementary nucleoside or nucleotide bases in a pair of oligonucleotides. The cumulative bonding, when sufficient, bonds the oligonucleotides to each other.

As used herein, the term "complementary" refers, in one embodiment, to the ability of a pair of nucleoside or nucleotide bases to specifically bond with each other through hydrogen bonding. For example, in DNA, Adenine (A) and Thymidine (T) are complementary bases, and Cytosine (C) and Guanine (G) are complementary bases. The same is true in RNA, except that Uracil (U) is complementary to Adenine (A).

As used herein, the term "oligonucleotide" refers, in one embodiment, to an oligomer or polymer of ribonucleic acid (RNA) or deoxyribonucleic acid (DNA), or mimetics thereof. The term encompasses oligomers and polymers that include naturally occurring bases, non-naturally occurring bases that function similar to natural bases, and combinations thereof.

As used herein, the term "polynucleotide" refers to an oligomer or polymer of RNA or DNA in the same manner as an "oligonucleotide". The difference between the two terms is merely one of relative size: a polynucleotide refers to a larger entity, which may contain one or more oligonucleotides.

In one embodiment, the term "homologous", refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. In another embodiment, if 6 of 10, of the positions in two sequences are matched or homologous then the two sequences are 60% homologous. In another embodiment, the DNA sequences ATTGCC and TATGGC share 50% homology. In one embodiment, a comparison is made when two sequences are aligned to give maximum homology.

In one embodiment, to determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology # of identical positions/total # of positions times 100). In another embodiment, the determination of percent homology between two sequences can be accomplished using a mathematical algorithm. In one embodiment, a non-limiting example of a mathematical algorithm utilized for the comparison of two sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs of Altschul, et al. (1990) J. Mol. Biol. 215:403-10. To obtain gapped alignments for comparison purposes, Gapped BLAST can be utilized as described in Altschul et al., (1997) Nucleic Acids Research 25(17):3389-3402. When utilizing BLAST and Gapped BLAST programs, the default parameters of the respective programs (e.g., XBLAST and NBLAST) can be used. In another embodiment, a non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used, in one embodiment. In another embodiment, programs which are equivalent in terms of the results they produce can be used.

In one embodiment, "protein" or "polypeptide" refers to an amino acid chain comprising multiple peptide subunits, and may, in one embodiment, include a full-length protein, oligopeptides, and fragments thereof, wherein the amino acid residues are linked by covalent peptide bonds. In one embodiment, a protein described in the present invention may comprise a polypeptide of the present invention. In one embodiment, a protein is a multimeric structure. In one embodiment, a protein of the present invention is a holotoxin.

The term "native" or "native sequence" refers to a polypeptide having the same amino acid sequence as a polypeptide that occurs in nature. A polypeptide is considered to be "native" in accordance with the present invention regardless of its mode of preparation. Thus, such native sequence polypeptide can be isolated from nature or can be produced by recombinant and/or synthetic means. The terms "native" and "native sequence" specifically encompass naturally-occurring truncated or secreted forms (e.g., an extracellular domain sequence), naturally-occurring variant forms (e.g., alternatively spliced forms) and naturally-occurring allelic variants of a polypeptide.

As used herein in the specification and in the examples section which follows the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Naturally occurring amino acids and non-conventional or modified amino acids which can be used with the present invention are well known in the art.

As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type tumor suppressor protein. "Equivalent proteins" and "equivalent polypeptides" refer to compounds that depart from the linear sequence of the naturally occurring proteins or polypeptides, but which have amino acid substitutions that do not change it's biologically activity. These equivalents can differ from the native sequences by the replacement of one or more amino acids with related amino acids, for example, similarly charged amino acids, or the substitution or modification of side chains or functional groups.

The polypeptide of the present invention can be of any size. As can be expected, the polypeptides can exhibit a wide variety of molecular weights, some exceeding 150 to 200 kilodaltons (kD). Typically, the polypeptides may have a molecular weight ranging from about 5,000 to about 100,000 daltons. Still others may fall in a narrower range, for example, about 10,000 to about 75,000 daltons, or about 20,000 to about 50,000 daltons. In one embodiment, the polypeptides have a molecular weight between 19 and 51 kD. In one embodiment, a polypeptide of the present invention is 298 amino acids. In another embodiment, a polypeptide of the present invention is 396 amino acids. In another embodiment, a polypeptide of the present invention is 301 amino acids. In one embodiment, a polypeptide of the present invention is between 250 and 450 amino acid residues long. In another embodiment, a polypeptide of the present invention is between 200 and 500 amino acid residues long. In another embodiment, a polypeptide of the present invention is between 275 and 425 amino acid residues long. In another embodiment, a polypeptide of the present invention is between 100 and 600 amino acid residues long.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

Amino acid sequence variants may be used in the compositions and methods of the present invention. In one embodiment, amino acid sequence variants can be produced by expressing the underlying DNA sequence in a suitable recombinant host cell, or by in vitro synthesis of the desired polypeptide, as discussed above. The nucleic acid sequence encoding a polypeptide variant is, in one embodiment, prepared by site-directed mutagenesis of the nucleic acid sequence encoding the corresponding native (e.g. human) polypeptide. In another embodiment, site-directed mutagenesis using polymerase chain reaction (PCR) amplification (see, for example, U.S. Pat. No. 4,683,195 issued 28 Jul. 1987; and Current Protocols In Molecular Biology, Chapter 15 (Ausubel et al., ed., 1991) is used. Other site-directed mutagenesis techniques are also well known in the art and are described, for example, in the following publications: Current Protocols In Molecular Biology, supra, Chapter 8; Molecular Cloning: A Laboratory Manual., $2^{nd}$ edition (Sambrook et al., 1989); Zoller et al., Methods Enzymol. 100:468-500 (1983); Zoller & Smith, DNA 3:479-488 (1984); Zoller et al., Nucl. Acids Res., 10:6487 (1987); Brake et al., Proc. Natl. Acad. Sci. USA 81:4642-4646 (1984); Botstein et al., Science 229: 1193 (1985); Kunkel et al., Methods Enzymol. 154:367-82 (1987), Adelman et al., DNA 2:183 (1983); and Carter et al., Nucl. Acids Res., 13:4331 (1986). Cassette mutagenesis (Wells et al., Gene 34:315 [1985]), and restriction selection mutagenesis (Wells et al., Philos. Trans. R. Soc. London SerA, 317:415) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The polypeptides of the invention can also be prepared by the combinatorial peptide library method disclosed, for example, in International Patent Publication PCT WO 92/09300. This method is particularly suitable for preparing and analyzing a plurality of molecules, that are variants of a given predetermined sequences, and is, therefore, particularly useful in identifying polypeptides with improved biological properties, which can then be produced by any technique known in the art, including recombinant DNA technology and/or chemical synthesis.

In one embodiment, a variant of a polypeptide, which in one embodiment, is a CdtB variant, is engineered to have reduced antigenicity.

In one embodiment, a fragment of a polypeptide, which in one embodiment, is a CdtB fragment, maintains its biological activity, which in one embodiment is a targeting function and in another embodiment, a downregulation of PIP3.

In one embodiment, "isoform" refers to a version of a molecule, for example, a protein, with only slight differences to another isoform of the same protein. In one embodiment, isoforms may be produced from different but related genes, or in another embodiment, may arise from the same gene by alternative splicing. In another embodiment, isoforms are caused by single nucleotide polymorphisms.

In some embodiments, any of the polypeptides or nucleic acids of and for use in the methods of the present invention will comprise a CdtB toxin subunit, or an isolated nucleic acid encoded said CdtB toxin subunit, in any form or embodiment as described herein. In some embodiments, any of the polypeptides or nucleic acids of and for use in the methods of the present invention will consist of either a CdtB toxin subunit or a Cdt holoxin, or an isolated nucleic acid encoded said CdtB toxin subunit or a Cdt holoxin of the present invention, in any form or embodiment as described herein. In some embodiments, the chimeric polypeptides or nucleic acids of this invention will consist essentially of a CdtB toxin subunit or a Cdt holoxin, or an isolated nucleic acid encoded said components of the present invention, in any form or embodiment as described herein. In some embodiments, the term "comprise" refers to the inclusion of other fragments, other antibodies, additional polypeptides, as well as inclusion of other proteins that may be known in the art. In some embodiments, the term "consisting essentially of" refers to a polypeptide or nucleic acid, which has the specific CdtB toxin subunit or Cdt holotoxin. However, other peptides may be included that are not involved directly in the utility of the toxin. In some embodiments, the term "consisting" refers to a toxin having the specific Cdt subunit(s) of the present invention, in any form or embodiment as described herein. In another embodiment, any composition or agent for use in the methods of the present invention will comprise an anti-CdtB antibody, a functional fragment of an anti-CdtB antibody, or a phosphatase inhibitor, or a combination thereof. In another embodiment a composition for use in the methods of the present invention will consist essentially of an anti-CdtB antibody, a functional fragment of an anti-CdtB antibody, or a phosphatase inhibitor, or a combination thereof. In another embodiment, a composition for use in the methods of the present invention will consist of an anti-CdtB antibody, a functional fragment of an anti-CdtB antibody, or a phosphatase inhibitor, or a combination thereof. Each of these is considered a separate embodiment of the present invention.

In another embodiment, methods and compositions of the present invention utilize a chimeric molecule, comprising a fusion of a recombinant chimeric polypeptide with a tag polypeptide that provides an epitope to which an anti-tag antibody can selectively bind. The epitope tag is placed, in other embodiments, at the amino- or carboxyl-terminus of the protein or in an internal location therein. The presence of such epitope-tagged forms of the chimeric polypeptide is detected, in another embodiment, using an antibody against the tag polypeptide. In another embodiment, inclusion of the epitope tag enables the recombinant chimeric polypeptide to be readily purified by affinity purification using an anti-tag antibody or another type of affinity matrix that binds to the epitope tag. Various tag polypeptides and their respective antibodies are known in the art. Examples include poly-histidine (poly-his) or poly-histidine-glycine (poly-his-gly) tags; the flu HA tag polypeptide and its antibody 12CA5 (Field et al., Mol. Cell. Biol., 8: 2159-2165 (1988)); the c-myc tag and the 8F9, 3C7, 6E10, G4, B7 and 9E10 antibodies thereto (Evan et al., Molecular and Cellular Biology, 5: 3610-3616 (1985)); and the Herpes Simplex virus glycoprotein D (gD) tag and its antibody (Paborsky et al., Protein Engineering, 3(6): 547-553 (1990)). Other tag polypeptides include the Flag-peptide (Hopp et al., BioTechnology, 6: 1204-1210 (1988)); the KT3 epitope peptide (Martin et al., Science, 255: 192-194 (1992)); a tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87: 6393-6397 (1990)). Methods for constructing fusion proteins are well known in the art, and are described, for example, in LaRochelle et al., J. Cell Biol., 139(2): 357-66 (1995); Heidaran et al., FASEB J., 9(1): 140-5 (1995); Ashkenazi et al., Int. Rev. Immunol., 10(2-3): 219-27 (1993) and Cheon et al., PNAS USA, 91(3): 989-93 (1994).

In another embodiment, the present invention provides a vector encoding a polypeptide comprising one or more cytolethal distending toxin (Cdt) subunits. In another embodiment, the present invention provides a vector encoding a polypeptide comprising a cytolethal distending toxin-B (CdtB).

In one embodiment, the nucleic acid encoding said Cdt subunit is inserted into a vector in one embodiment, such that the Cdt subunit is expressed. In another embodiment, the invention provides isolated nucleic acid molecules encoding Cdt of the present invention. In another embodiment, the invention provides vectors comprising such nucleic acid molecules, and recombinant host cells transformed with such vectors.

In one embodiment, a "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a nucleic acid of the present invention.

In one embodiment, the vectors of the formulations and methods of the instant invention comprise a nucleic acid sequence. As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotide. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the term "nucleic acid" or "oligonucleotide" refers to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The nucleic acids can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its solubility, or binding affinity to complementary sequences. These nucleic acids may comprise the vector, the expression cassette, the promoter sequence, the gene of interest, or any combination thereof. In another embodiment, its lipophilicity may be modified, which, in turn, will reflect changes in the systems employed for its delivery, and in one embodiment, may further be influenced by whether such sequences are desired for retention within, or permeation through the skin, or any of its layers. Such considerations may influence any compound used in this invention, in the methods and systems described.

The term "promoter" means a nucleotide sequence that, when operably linked to a DNA sequence of interest, promotes transcription of that DNA sequence.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. Variations in DNA sequences, which are caused by point mutations or by induced modifications (including insertion, deletion, and substitution) to enhance the activity, half-life or production of the polypeptides encoded thereby, are also encompassed in the invention.

The formulations of this invention may comprise nucleic acids, in one embodiment, or in another embodiment, the methods of this invention may include delivery of the same, wherein, in another embodiment, the nucleic acid is a part of a vector.

The efficacy of a particular expression vector system and method of introducing nucleic acid into a cell can be assessed by standard approaches routinely used in the art as described hereinbelow.

As will be appreciated by one skilled in the art, a fragment or derivative of a nucleic acid sequence or gene that encodes for a protein or peptide can still function in the same manner as the entire wild type gene or sequence. Likewise, forms of nucleic acid sequences can have variations as compared to wild type sequences, nevertheless encoding the protein or peptide of interest, or fragments thereof, retaining wild type function exhibiting the same biological effect, despite these variations. Each of these represents a separate embodiment of this present invention.

In one embodiment, the term "vector" or "expression vector" refers to a carrier molecule into which a nucleic acid sequence can be inserted for introduction into a cell where it can be replicated. In one embodiment, the nucleic acid molecules are transcribed into RNA, which in some cases are then translated into a protein, polypeptide, or peptide. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. In one embodiment the vector may be a shuttle vector, which in one embodiment can propagate both in prokaryotic and eukaryotic cells, or in another embodiment, the vector may be constructed to facilitate its integration within the genome of an organism of choice. The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus. In one embodiment, a vector is a plasmid.

In one embodiment, lymphocytes are the primary in vivo targets of Cdt; based in part upon their exquisite sensitivity to toxin-induced cell cycle arrest. In another embodiment, the underlying basis for this heightened sensitivity to the toxin is related to a combination of CdtB-associated lipid phosphatase activity and lymphocyte dependence upon PI-3,4,5-P3. In one embodiment, CdtB, like SHIP1 and PTEN, mediates its regulatory effects by dephosphorylating PI-3,4,5-P3, thereby modulating the activity of pleckstrin homology containing proteins such as Akt in another embodiment. Accordingly, provided herein is a method of modulating the effect of Akt in a lymphoyte, comprising the step of contacting the lymphocyte with a composition comprising CdtB toxin, or its mutant, in a therapeutically effective amount to modulate the effects of Akt.

In one embodiment, antigenic and mitogenic activation leading to clonal expansion of lymphocytes is dependent upon increases in PI-3,4,5-P3 and subsequent activation of the Akt pathway. This mechanism of action accounts in another embodiment, for the heightened sensitivity of leukemic cells to Cdt because mutations of PTEN and/or SHIP1 appears to be common feature of cells such as Jurkat. In one embodiment, the mechanism of action for Cdt in lymphocytes, and other cell types in other embodiments, involves the depletion of PI-3,4,5-P3 and a concomitant inactivation of the Akt pathway. In one embodiment, inactivation of Akt leads to both cell cycle arrest and the activation of the apoptotic cascade, events that are also associated with the action of Cdt.

In one embodiment, the methods described herein, which comprise the step of administering to the subject a composition comprising an isolated CdtB toxin or its mutant, further comprises PI-(3,4,5)-$P_3$ in these compositions. In another embodiment, the compositions further comprise an enzyme specific for PI-(3,4,5)-$P_3$, wherein the enzyme specific for PI-(3,4,5)-$P_3$, is PTEN, SHIP1, SHIP2 or a combination thereof.

The term "about" as used herein means in quantitative terms plus or minus 5%, or, in another embodiment, plus or minus 10%, or, in another embodiment, plus or minus 15%, or, in another embodiment, plus or minus 20%.

The term "subject" refers, in one embodiment, to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

In one embodiment, the compositions and methods of the present invention are for use in human subjects, while in another embodiment, they are for use in mammalian subjects. In one embodiment, the subject is an animal subject, which in one embodiment, is murine, bovine, canine, feline, equine, porcine, etc. In one embodiment, the term "mammal" or "mammalian" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. In one embodiment, the compositions and methods of the present invention are effective in male subjects. In another embodiment, the compositions and methods of the present invention are effective in female subjects.

In one embodiment, "treating" refers to either therapeutic treatment or prophylactic or preventative measures, wherein the object is to prevent or lessen the targeted condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

"Contacting," in one embodiment, refers to directly contacting the target cell with a chimeric polypeptide of the present invention. In another embodiment, "contacting" refers to indirectly contacting the target cell with a chimeric polypeptide of the present invention. Thus, in one embodiment, methods of the present invention include methods in which the subject is contacted with a chimeric polypeptide which is brought in contact with the target cell by diffusion or any other active transport or passive transport process known in the art by which compounds circulate within the body.

In one embodiment, the methods of the present invention comprising the step of administering a composition of the present invention to a subject in need. In one embodiment, "administering" refers to directly introducing into a subject by injection or other means a composition of the present invention. In another embodiment, "administering" refers to contacting a cell of the subject's immune system with a composition of the present invention. In one embodiment, the compositions of the present invention are administered chronically, while in another embodiment, they are administered intermittently.

In one embodiment, "chronic" administration refers to administration of the agent(s) in a continuous mode as opposed to an acute mode, so as to maintain a desired effect or level of agent(s) for an extended period of time.

In one embodiment, "intermittent" administration is treatment that is not consecutively done without interruption, but rather is periodic in nature.

Administration "in combination with" or "in conjunction with" one or more further therapeutic agents includes simultaneous (concurrent) and consecutive administration in any order.

An "effective amount" is an amount sufficient to effect beneficial or desired therapeutic (including preventative) results. An effective amount can be administered in one or more administrations.

In another embodiment, of the present invention, the therapeutic composition described herein at therapeutically effective concentrations or dosages may be combined with a pharmaceutically or pharmacologically acceptable carrier, excipient or diluent, either biodegradable or non-biodegradable.

The invention includes "pharmaceutically acceptable salts" of the compound of this invention, which may be produced, in one embodiment, using an amino-substituted compound and an organic and inorganic acids, for example, citric acid and hydrochloric acid. Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters. As used herein, "pharmaceutically acceptable salt" refers to, in one embodiment, those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in J. Pharmaceutical Sciences, 1977, 66: 1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzene-sulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary as ammonium, and mine cations, including, but not limited to ammonium, tetramethylammonium, tetraethylammonium, methylamine, dimethylamine, trimethylamine, triethylamine, ethylamine, and the like.

This invention provides, in other embodiments, pharmaceutical products of the compounds of this invention. The term "pharmaceutical product" refers, in other embodiments, to a composition suitable for pharmaceutical use (pharmaceutical composition), for example, as described herein.

In one embodiment this invention provides a pharmaceutical composition comprising the compounds of this invention.

In one embodiment the composition further comprises a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution, a spray, a dermal patch or a suppository. In one embodiment the composition is in the form of a capsule. In one embodiment the composition is in a form suitable for oral, intravenous, intraarterial, intramuscular, intracranial, intranasal, subcutaneous, parenteral, transmucosal, transdermal, intratumoral or topical administration. In one embodiment the composition is a controlled release composition. In one embodiment the composition is an immediate release composition. In one embodiment the composition is a liquid dosage form. In one embodiment the composition is a solid dosage form. In one embodiment the composition further comprises an additional antineoplastic compound, an immunotherapeutic agent or an additional drug.

In another embodiment, this invention provides a composition comprising a compound of this invention. In one embodiment this invention provides a pharmaceutical composition comprising the compounds of the present invention.

In one embodiment the composition further comprising a carrier, diluent, lubricant, flow-aid, or a mixture thereof. In one embodiment the composition is in the form of a pellet, a tablet, a capsule, a solution, a suspension, a dispersion, an emulsion, an elixir, a gel, an ointment, a cream, an I.V. solution or a suppository. In one embodiment the composition is in the form of a capsule.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

In one embodiment the composition is in a form suitable for oral, intravenous, intraarterial, intramuscular, intracranial, intranasal, subcutaneous, parenteral, transmucosal, transdermal, rectally, intracisternally, intravaginally, intraperitoneally, topically (as by powders, ointments, dermal patches, sprays or drops), bucally, or as an oral or nasal spray. The term "parenteral" administration as used herein refers to modes of administration which include intravenous, intramuscular, intraperitoneal, intrathecally, intrasternal, subcutaneous and intraarticular injection and infusion.

In one embodiment the composition can be administered to humans and other animals. In one embodiment the composition is a controlled release composition. In one embodiment the composition is an immediate release composition. In one embodiment the composition is a liquid dosage form. In one embodiment the composition is a solid dosage form. In one embodiment the composition further comprising an antineoplastic compound, an immunotherapeutic agent or a drug. In one embodiment, the compositions of this invention, which comprise a polymer of this invention is biocompatible, and in another embodiment, may comprise pharmaceutically acceptable carriers or excipients, such as disclosed in Remington's Pharmaceutical Sciences, Mack Publishing Company, Easton, Pa., USA, 1985. These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

In one embodiment, administration of the compounds of the invention may be by inhalation for intranasal and/or intrapulmonary delivery. For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

In some cases, in order to prolong the effect of the compounds as drugs, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are, in one embodiment, suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the polymer compound of the present invention, stabilizers, preservatives, excipients, and the like. In one embodiment, the lipids may be natural or synthetic phospholipids or a combination thereof.

Methods to form liposomes are known in the art. See, for example, Prescott, Ed., Methods in Cell Biology, Volume XIV, Academic Press, New York, N.Y. (1976), p. 33 et seq.

The compounds of the present invention can also be administered as dendrimers, as functional groups on a dendrimer or trapped inside a dendrimer. As known in the art, dendrimers are repeatedly branched molecules. Their core structure is a molecule with at least two, and preferably more identical functional groups. The functional groups on this core molecule serve as an anchor for molecules bearing typically at least three of the same or similar functional groups. A layer of molecules can be bound to the first core molecule thus forming the first generation of the dendrimer. Since these molecules posses the same functional groups as the core molecules, they can bind an additional layer of molecules forming the second generation of the dendrimer. This scheme is then repeated until the desired number of generations is achieved. This repetition forms a branched structure in which each generation contains more molecules than the previous one. The branched nature of the dendrimer is the result of the branching ability of each molecule. The branching ability is reflected by the multiple functional groups of each molecule. Similar to a tree (which is the origin of the name), the number of branches grows from generation to generation. Compounds encapsulated in dendrimers can be slow-released into the environment, thus providing an advantage for various therapies.

In one embodiment compounds of the present invention can be mixed with a polymer and can be administered with a polymer or a polymeric particle. Similar to dendritic structures described herein above, polymers or polymeric particles can provide controlled release of the drug or the compound trapped in it.

Compounds of this invention can be bound to microparticles or nanoparticles and administered in this form. The micro/nano particles can be organic or inorganic. The compounds can become in contact with the desired tissue or area, they can be released from the particle by a cleaving agent or by the interaction of radiation with the particles. One aspect of radiation-induced release is a drug release that is induced by particle heating. Particles may further comprise a marker which can help in detecting the spatial location of the drug. Markers can help the controlled activation of the drug by assessing the location of the particle, and inducing release of the drug accordingly.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

The pharmaceutical compositions of the present invention can be used in both veterinary medicine and human therapy. The magnitude of a prophylactic or therapeutic dose of the pharmaceutical composition of the invention will vary with the severity of the condition to be treated and the route of administration. The dose, and perhaps the dose frequency, will also vary according to the age, body weight, and response of the individual patient.

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

In one embodiment, the compounds or compositions of this invention are used as a drug. In one embodiment, the term "drug" refers to a substance applicable for use in the diagnosis, or in another embodiment, cure, or in another embodiment, mitigation, or in another embodiment, treatment, or in another embodiment, prevention of a disease, disorder, condition or infection. In one embodiment, the term "drug" refers to any substance which affects the structure or function of the target to which it is applied.

In another embodiment, the term "drug" refers to a molecule that alleviates a symptom of a disease or disorder when administered to a subject afflicted thereof.

In another embodiment, compounds of this invention have a therapeutic effect. In one embodiment, the term "therapeutic", refers to a molecule, which when provided to a subject in need, provides a beneficial effect.

In one embodiment, the effective amounts of compounds of this invention given to a subject is tailored to the subject needs and to the condition treated. In one embodiment, compounds are given in an administration protocol in a variety of dose ranges depending on the particular need of the patient. One such suitable dose range is from 0.01 μg to 400 μg. Another suitable dose range is administered on a daily basis per kilogram of body weight, the dose ranges being from 0.001 μg/kg/day to 5.0 μg/kg/day. Another dosing regimen calls for a high dosage, generally 10 μg/dose or greater up to 400 μg/dose or greater, given episodically or intermittently. The protocol or dosage regimen in accordance with the present invention provides an improved therapeutic index. In an episodic dosing, a lower quantity of active agent might be needed.

In one embodiment, compositions of the present invention can be formulated for treating a subject according to personalized medicine. In one embodiment, personalized medicine describes the use of information and data from a patient's genotype, or level of gene expression to stratify disease, select a medication, provide a therapy, or initiate a preventative measure that is particularly suited to that patient at the time of administration. In addition to genetic information, other factors, including imaging, laboratory, and clinical information about the disease process or the patient play an equally important role. Personalized medicine is directed toward the possibility to give the appropriate drug, at the appropriate dose, to the appropriate patient, at the appropriate time. The benefits of this approach are in its accuracy, efficacy, safety and speed. Personalized medicine is a new approach to drug development with the potential of effective diagnosis, therapeutics, and patient care. Personalized medicine develops patient-specific tests that monitor the effectiveness of treatment and that can identify the recurrence of a disease in an early stage.

In one embodiment, the compositions of the present invention may be administered with other treatments for infectious and/or proliferative disorders known in the art.

In one embodiment, the article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The container may also be an inhalation device such as those discussed above. At least one active agent in the composition is a fusion compound of the invention. The label or package insert indicates that the composition is used for treating the condition of choice, such as a lymphoproliferative disease, a hypersensitivity disease, an inflammatory disease, Cdt toxin poisoning, or an infectious disease discussed above. The article of manufacture may further comprise a further container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In one embodiment, compositions and methods of the present invention for treating a disease may be used to treat a related disorder and vice versa.

The following examples are presented in order to more fully illustrate the preferred embodiments of the invention. They should in no way be construed, however, as limiting the broad scope of the invention.

EXAMPLES

Materials and Methods

Cell Lines and Analysis of Cell Cycle

The human leukemic T cell lines Jurkat, CEM and Molt were maintained in RPMI 1640 supplemented with 10% FCS, 2 mM glutamine, 10 mM HEPES, 100 U/ml penicillin and 100 μg/ml streptomycin. HUT78 cells were maintained in Isoves modified Dulbecco medium containing 4 mM L-glutamine and 20% FCS. Cells were harvested in mid-log growth phase and plated at $5\times10^5$ cells/ml, or as indicated, in 24-well tissue culture plates. The cells were exposed to medium, Cdt peptides or CdtABC and incubated for 18 hr. To measure Cdt-induced cell cycle arrest, Jurkat cells were washed and fixed for 60 min with cold 80% ethanol (27). After washing, the cells were stained with 10 μg/ml propidium iodide containing 1 mg/ml RNase (Sigma Chemical Co; St. Louis, Mo.) for 30 min. Samples were analyzed on a Becton-Dickinson FacstarpLus flow cytometer (BD Biosciences; San Jose, Calif.). Propidium iodide fluorescence was excited by an argon laser operating at 488 nm and fluorescence measured with a 630/22 nm bandpass filter using linear amplification. A minimum of 15,000 events were collected on each sample; cell cycle analysis was performed using Modfit (Verity Software House; Topsham, Me.).

Construction and Expression of CdtB Mutants

Amino acid substitutions were introduced into the CdtB gene by in vitro site-directed mutagenesis using oligonucleotide primer pairs containing appropriate base changes (Table 1). Site-directed mutagenesis was performed using the QuikChange II site-directed mutagenesis kit (Stratagene) according to the manufacturers directions. Amplification of the mutant plasmid was carried out using PfuUltra HF DNA polymerase (Stratagene) and pGEMCdtB as a template; construction and characterization of this plasmid was previously described. All mutants were verified by DNA sequencing. Expression of the plasmids and purification of the mutant peptides is described below.

TABLE 1

CdtB mutant constructs

| Plasmid | Primer | SEQ ID NO: | Sequence[a] |
|---|---|---|---|
| pGEMCdtB$^{H160Q}$ | P1 | 11 | GTATTTTTTACAGTGCA**G**GCTTTGGCCACA |
| | P2 | 12 | TGTGGCCAAAGC**C**TGCACTGTAAAAAATAC |
| pGEMCdtB$^{H274Q}$ | P1 | 13 | CAAATTACATCCGATCA**G**TTTCCTGTTAGTTTTGT |
| | P2 | 14 | ACAAAACTAACAGGAAA**C**TGATCGGATGTAATTTG |
| pGEMCdtB$^{R117A}$ | P1 | 15 | GATGTTGGGGCAAAC**GC**AGTGAACTTAGCTATCG |
| | P2 | 16 | CGATAGCTAAGTTCACT**GC**GTTTGCCCCAACATC |

TABLE 1-continued

CdtB mutant constructs

| Plasmid | Primer | SEQ ID NO: | Sequence[a] |
|---|---|---|---|
| pGEMCdtB$^{D199S}$ | P1 | 17 | GATGGTTGTTGGTAGTTTCAATCGTGCGCCGGT |
| | P2 | 18 | ACCGGCGCACGATTGAAACTACCAACAACCATC |
| pGEMCdtB$^{A163R}$ | P1 | 19 | CAGTGCATGCTTTGCGCACAGGTGGTTCTGATGCGG |
| | P2 | 20 | CCGCATCAGAACCACCTGTGCGCAAAGCATGCACTG |
| pGEMCdtB$^{A163N}$ | P1 | 21 | CAGTGCATGCTTTGAACACAGGTGGTTCTGATGCGG |
| | P2 | 22 | CCGCATCAGAACCACCTGTGTTCAAAGCATGCACTG |

[a]Underlined letters in the sequence indicate nucleotide substitutions.

Expression and Purification of Cdt Peptides and Cdt Holotoxin (CdtABC)

Construction and expression of the plasmid containing wildtype CdtB gene (pGEMCdtB) was previously described (27). In vitro expression of Cdt peptides and CdtB mutants was performed as previously described using the Rapid Translation System (RTS 500 ProteoMaster; Roche Applied Science, Reactions were run according to the manufacturers specification (Roche Applied Science) using 10-15 μg of template DNA. After 20 hrs at 30° C., the reaction mix was removed and the expressed Cdt peptides were purified by nickel affinity chromatography as described [Shenker, B. J., D. Besack, T. L. McKay, L. Pankoski, A. Zekavat, and D. R. Demuth. 2005. Induction of cell cycle arrest in lymphocytes by *Actinobacillus actinomycetemcomitans* cytolethal distending toxin requires three subunits for maximum activity. *J. Immunol.* 174: 2228-2234].

Construction and expression of the plasmid containing the Cdt genes for the holotoxin (pUCAaCdtABC$^{his}$) has previously been reported (28). The plasmid was constructed so that the Cdt genes were under control of the lac promotor and transformed into *E. coli* DH5α. Cultures of transformed *E. coli* were grown in IL LB broth and induced with 0.1 mM IPTG for 2 hr; bacterial cells were harvested, washed and resuspended in 50 mM Tris (pH 8.0). The cells were frozen overnight, thawed and sonicated. The histidine-tagged peptide holotoxin was isolated by nickel affinity chromatography as previously described [Shenker, B. J., R. H. Hoffmaster, T. L. McKay, and D. R. Demuth. 2000. Expression of the cytolethal distending toxin (Cdt) operon in *Actinobacillus actinoimycetemcomitans*: evidence that the CdtB protein is responsible for G2 arrest of the cell cyclein human T-cells. *J. Immunol.* 165:2612-2618].

Phosphatase Assay

Phosphatase activity was assessed by monitoring the dephosphorylation of PI-3,4,5-$P_3$ as described by Maehama et al [Maehama, T., G. Taylor, J. Slama, and J. Dixon. 2000. A sensitive assay for phosphoinositide phosphatases. *Analytical Biochemistry* 279:248-2501. Briefly, the reaction mixture (20 μl) consisted of 100 mM Tris-HCl (pH 8.0), 10 mM dithiothreitol, 0.5 mM diC16-phosphatidylserine (Avanti), 25 μM PI-3,4,5-$P_3$ (diC16; Echelon) and the indicated amount of CdtB, CdtABC or PTEN (kindly provided by Gregory Taylor). Appropriate amounts of lipid solutions were deposited in 1.5 ml tubes, organic solvent removed, the buffer added and a lipid suspension formed by sonication. For experiments to determine substrate specificity, PI-3,4,5-$P_3$ was replaced by the indicated phosphatidylinositol phosphate (Echelon). Phosphatase assays were carried out at 37° C. for 30 min; the reactions were terminated by the addition of 15 μl of 100 mM N-ethylmaleimide. Inorganic phosphate levels were then measured using a malachite green assay. Malachite green solution (Biomol Green; Biomol) was added to 100 μl of the enzyme reaction mixture and color was developed for 20 min at RT. Absorbance at 650 nm was measured and phosphate release quantified by comparison to inorganic phosphate standards.

Analysis of CdtB-Mediated Product Formation

Inositol lipids were separated by thin layer chromatography. Silica gel G plates were dipped in boric acid (5% in methanol) and then dried. They were then spotted with the lipid samples dissolved in chloroform/methanol/water (1/2/0.1) together with solutions containing the standard inositol lipids phosphatidyl 4,5 bisphosphate, phosphatidyl 3,4 bisphosphate, phosphatidyl 3,5bis phosphate, phosphatidyl 3,4,5 trisphosphate, and phosphatidyl inositol. The plates were eluted with solutions containing propyl acetate/isopropanol/ethanol/ammonia/water (15/45/16/9/35), dried, and sprayed with solution containing CuSO4/H3PO4 (8%/10%), and air dried again. Plates were then heated to 70° C. then to 155° C. to visualize the lipids.

DNase Assay

CdtB peptides were assessed for DNase activity by monitoring changes in electrophoretic mobility of supercoiled plasmid DNA as described by Elwell and Dreyfus [Elwell, C. A., and L. A. Dreyfus. 2000. DNase I homologous residues in CdtB are critical for cytolethal distending toxin-mediated cell cycle arrest. *Molecular Microbiology* 37:952-963]. Briefly, supercoiled pUC19 (1 μg per reaction) was incubated with CdtB, CdtB mutants or bovine DNase I for 2 hrs at 37° C. in a buffer containing 25 mM Hepes (pH 7.0), 10 mM $MgCl_2$ and 5 mM $CaCl_2$. The reaction was stopped by adding 10 mM EDTA (final concentration). The samples were then loaded onto 1% agarose gel and subjected to electrophoresis in TBE buffer; gels were stained with ethidium bromide and analyzed by digital scanning densitometry.

Measurement of Cellular PI-3,4,5-$P_3$ Content

Jurkat cells ($5\times10^5$/ml) were incubated in the presence of medium or Cdt holotoxin for 30-240 min. Replicate cultures ($1\times10^7$ cells) were pooled and harvested. The cell pellet was treated with cold 0.5 TCA for 5 min, centrifuged and the pellet washed twice with 5% TCA containing 1 mM EDTA. Neutral lipids were extracted twice with methanol:chloroform (2:1) at RT. Acidic lipids were extracted with 2.25 ml methanol:chloroform:12M HCl (80:40:1) for 15 min at RT; the samples were centrifuged for 5 min and the supernatant recovered. The supernatant was then treated with 0.75 ml chloroform and 1.35 ml 0.1 M HCl and centrifuged to separate organic and aqueous phases; the organic phase was collected and dried. The dried lipids were resuspended in 120 μl 50 mM Hepes buffer (pH 7.4) containing 150 mM NaCl and 1.5% sodium cholate, and left overnight at 4° C. PI-3,4,5-$P_3$ levels were then determined using a commercially available competitive ELISA according to the manufacturers directions (PIP3 Mass ELISA Kit; Echelon).

Structural Comparisons

Multiple structural alignment of CdtB from *A. actinomycetemcomitans* with inositol polyphosphate 5-phosphatase and DNase I was made using MUSTANG (30-33). Positional sequence conservation of CdtB was derived from combined alignments of CdtB and inositol polyphosphate 5-phosphatase homologs and residue conservation was determined. Conservation indices were converted to colors (red, most conserved; green, intermediate; blue, least conserved) and mapped onto the CdtB structure using Bobscript.

Example 1

CdtB Shares Catalytic Residues and Similar Reaction Mechanism with the Large Group of Functionally Diverse $Mg^{2+}$-Dependent Phosphoesterases It has been proposed, based on sequence comparisons, that CdtB shares catalytic residues and similar reaction mechanism with the large group of functionally diverse $Mg^{2+}$-dependent phosphoesterases. DNase I was the first structurally characterized member of this diverse enzyme superfamily as well as subsequent structural characterization of inositol polyphosphate 5-phosphatases and CdtB, which confirmed the initial prediction. An alignment of these three structures shows striking conservation of catalytic and divalent ion-chelating residues, despite low overall sequence identity (FIG. 1). As a general rule, all enzymes in this superfamily hydrolyze phosphate esters and their exact function depends on what substrate(s) can be accommodated in the active site. CdtB was originally characterized as a DNase-like enzyme and the putative phosphatidylinositol phosphatase activity was never formally tested despite its weak nuclease activity.

Example 2

CdtB Exhibits Phosphatase Activity

Figure 2:
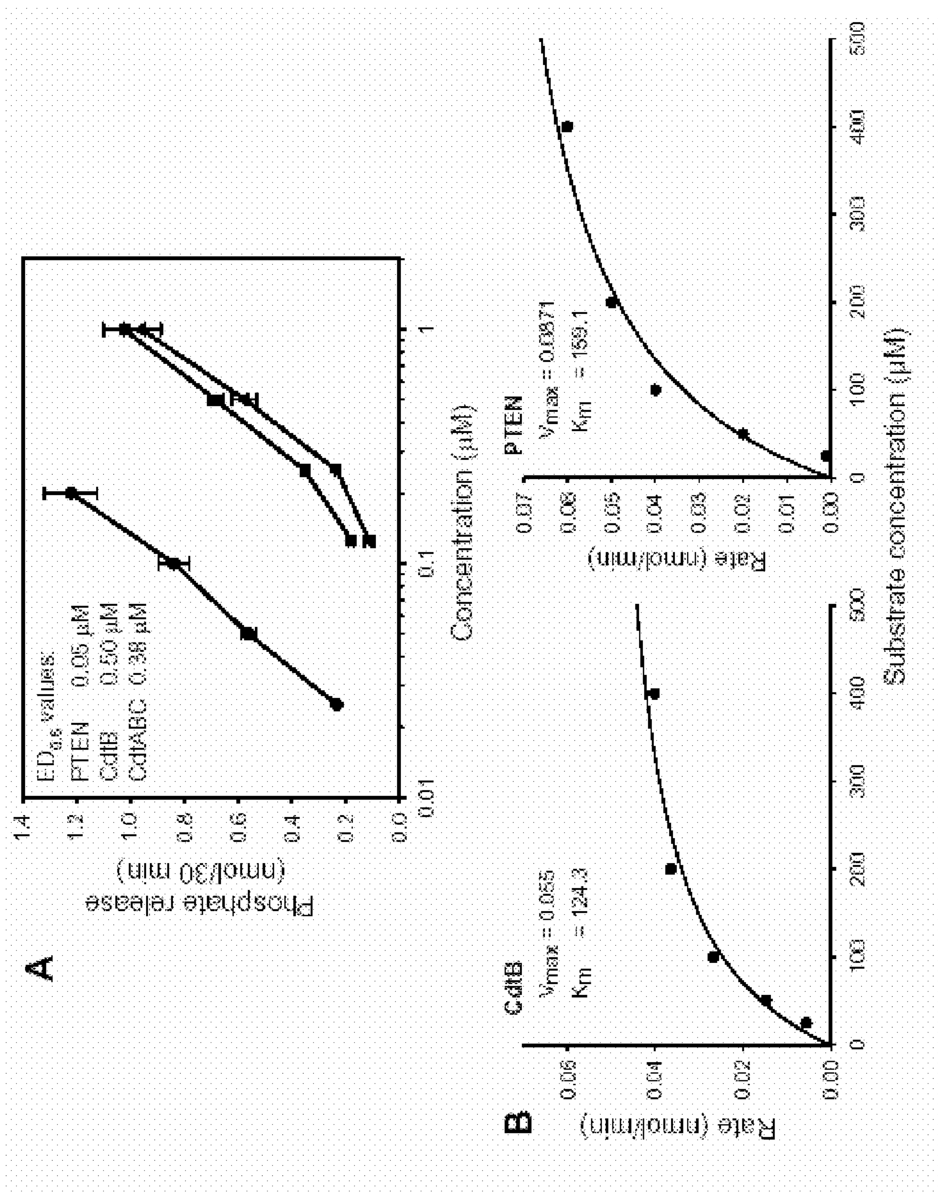
FIG. 2 shows that CdtB exhibits PI-3,4,5-$P_3$ phosphatase activity. As shown in panel A, varying amounts of CdtB (triangles), CdtABC (squares) and PTEN (circles) were assessed for their ability to hydrolyze PI(3,4,5)-$P_3$ as described in Materials and Methods. The amount of phosphate release was measured using a malachite green binding assay. Data are plotted as phosphate release (nmol/30 min; mean±S.D) versus protein concentration; numbers shown are $ED_{0.5}$ values defined as the concentration required to induce approximately 50% (0.5 nmol) phosphate release under these assay conditions. Panel B shows the rate of CdtB (0.5 μM) and PTEN (0.1 μM) mediated phosphate release in the presence of varying concentrations of PI-3,4,5-$P_3$ was assessed. Data were analyzed using Michaelis-Menten kinetics. The Km values for CdtB and PTEN were 124.3 and 159.1 μM, respectively; Vmax were 0.55 nmol/min (CdtB) and 0.087 nmol/min (PTEN)

CdtB was initially assessed for its ability to dephosphorylate PI-3,4,5-$P_3$. As shown in FIG. 2A, CdtB exhibits dose-dependent (0.2-1.0 μM) phosphate release which ranged from 0.1 to 0.9 nmol in the presence of 0.2 and 1.0 μM CdtB, respectively. It should be noted that CdtA and CdtC failed to exhibit phosphatase activity under identical conditions (data not shown). The Cdt holotoxin (CdtABC), containing all three subunits, exhibited dose-dependent activity similar to that of CdtB. $ED_{0.5}$ values [concentration required to catalyze 0.5 nmol phosphate release] were calculated; the $ED_{0.5}$ for CdtB and the holotoxin were 0.5 μM and 0.38 μM, respectively. For comparative purposes, PTEN was also assessed for activity. PTEN exhibited dose-dependent (0.02-0.2 μM) phosphate release; thus PTEN was determined to be approximately ten times more active then CdtB with an $ED_{0.5}$ of 0.05 μM. To further explore the propensity of CdtB to act as a phosphatidylinositol phosphatase, a Michaelis-Menton relationship was presumed and $K_m$ and $V_{max}$ values were determined with respect to cleavage of PI-3,4,5-$P_3$ and compared to a similar analysis of PTEN (FIG. 2B). By this analysis, both CdtB and PTEN demonstrated similar $K_m$ values of 124.3 and 159.1 μM, respectively. $V_{max}$ values were 0.055 nmol/min for 0.5 μM CdtB and 0.087 nmol/min for 0.1 μM PTEN. Thus CdtB exhibits PI-3,4,5-$P_3$ phosphatase activity that is comparable to that of PTEN.

Example 3

Figure 3:
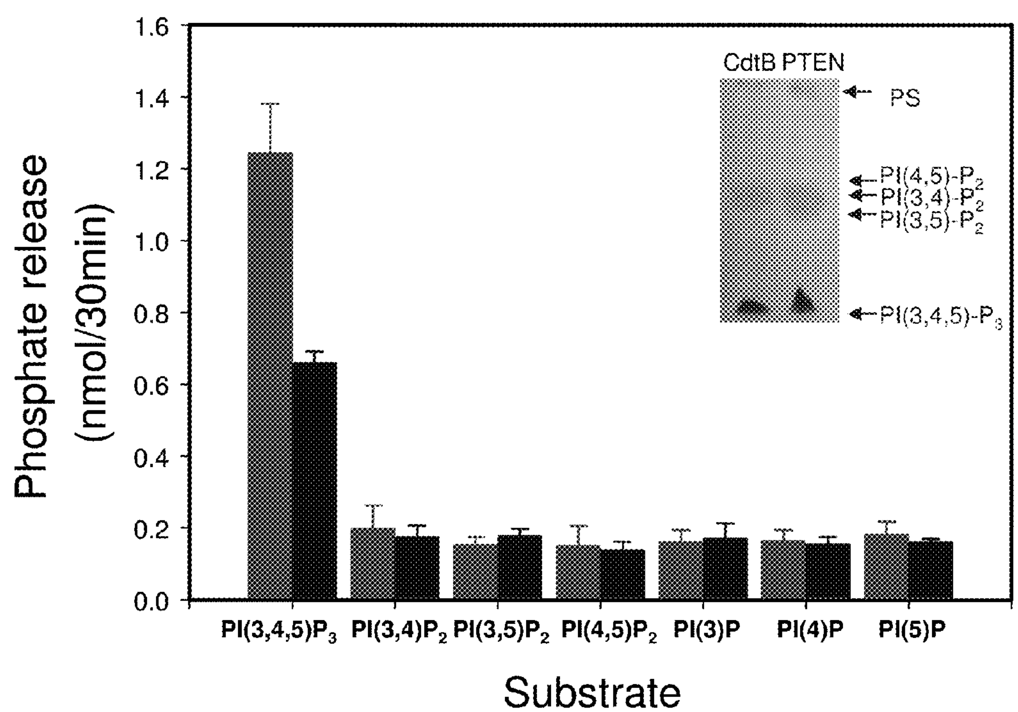
FIG. 3 shows analysis of substrate specificity and product formation for both CdtB and PTEN. CdtB (0.5 μM; solid bars) and PTEN (0.1 μM; open bars) were incubated for 30 min in presence of liposomes containing one of the phosphatidylinositol phosphates shown. Data are plotted as phosphate release (nmol/30 min; mean±S.D.) for each substrate. It should be noted that no phosphate release was observed in presence of phosphatidylserine alone. Inset shows results from TLC analysis of product formation following PI-3,4,5-$P_3$ hydrolysis in the presence of 0.5 μM CdtB or 0.1 μM PTEN.
Figure 4:
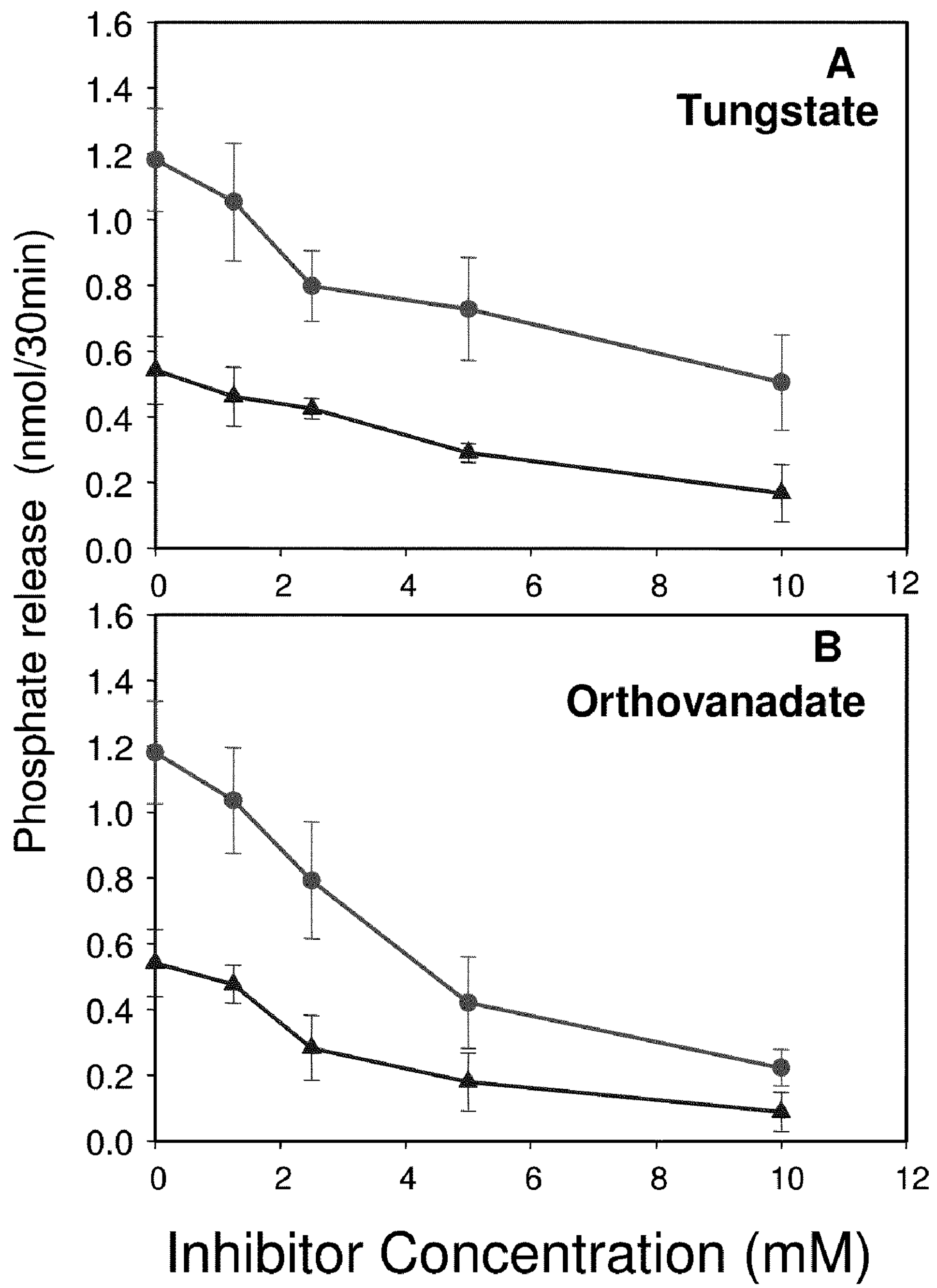
FIG. 4 shows effect of phosphatase inhibitors on CdtB-mediated hydrolysis of PI-3,4,5-$P_3$. CdtB (0.5 μM; triangles) and PTEN (0.1 μM; circles) were incubated with liposomes containing PI-3,4,5-$P_3$ in the presence of varying concentrations of tungstate or orthovanadate for 30 min. Phosphate release was measured using the malachite green binding assay. Results are plotted as phosphate release (nmol/30 min; mean±S.D.) versus inhibitor concentration (mM)

Lipid Moiety is Critical for CdtB Phosphatase Activity with PI-3,4,5-$P_3$ as the Substrate CdtB substrate specificity was assessed using several different phosphoinositides (PI). Experiments indicated that the lipid moiety was critical for CdtB phosphatase activity when PI-3,4,5-$P_3$ was used as a substrate; therefore, all PIs contained di-$C_{1-6}$ acyl side chains were tested. The PIs were incorporated into a lipid bilayer with phosphatidylserine as the carrier lipid. As shown in FIG. 3, CdtB-catalyzed phosphate release only occurred in the presence of PI-3,4,5-$P_3$; neither phosphatidylinositol diphosphates or monophosphates were able to serve as a substrate. PTEN exhibited substrate specificity for PI-(3,4,5)-$P_3$ identical to CdtB. In other experiments, it was also determined that CdtB was unable to dephosphorylate inositol triphosphate or inositol tetrakisphosphate. It should also be noted that CdtB did not exhibit detectable protein phosphatase activity when the synthetic substrate, pNPP, was employed. Additional similarities between PTEN and CdtB were observed with respect to susceptibility to the phosphatase inhibitors, tungstate and orthovanadate. As shown in FIG. 4, tungstate reduced CdtB phosphatase activity in a dose-dependent fashion; phosphatase activity was reduced 15% at 1 mM and 70% at 10 mM tungstate. Likewise, orthovanadate inhibited CdtB by 10% at 1 mM and 85% at 10 mM. PTEN exhibited similar dose-dependent sensitivity to these inhibitors. It should be noted that molybdate failed to inhibit CdtB or PTEN. In order to determine whether CdtB is a 3- or 5-phosphatase, product formation was assessed using thin layer chromatography. While both CdtB and PTEN share many properties, they differ with respect to the product produced. Whereas PTEN is specific for dephosphorylation at the D3 position of the inositol ring yielding PI-(4,5)-$P_2$, CdtB appears to be specific for the D5 position producing PI-(3,4)-$P_2$ (FIG. 3, insert) suggesting that CdtB activity may more accurately reflect that of an inositol 5-phosphatase similar to SHIP.

Example 4

CdtB Mutants Exhibit Reduced Phosphatase Activity

Figure 5:
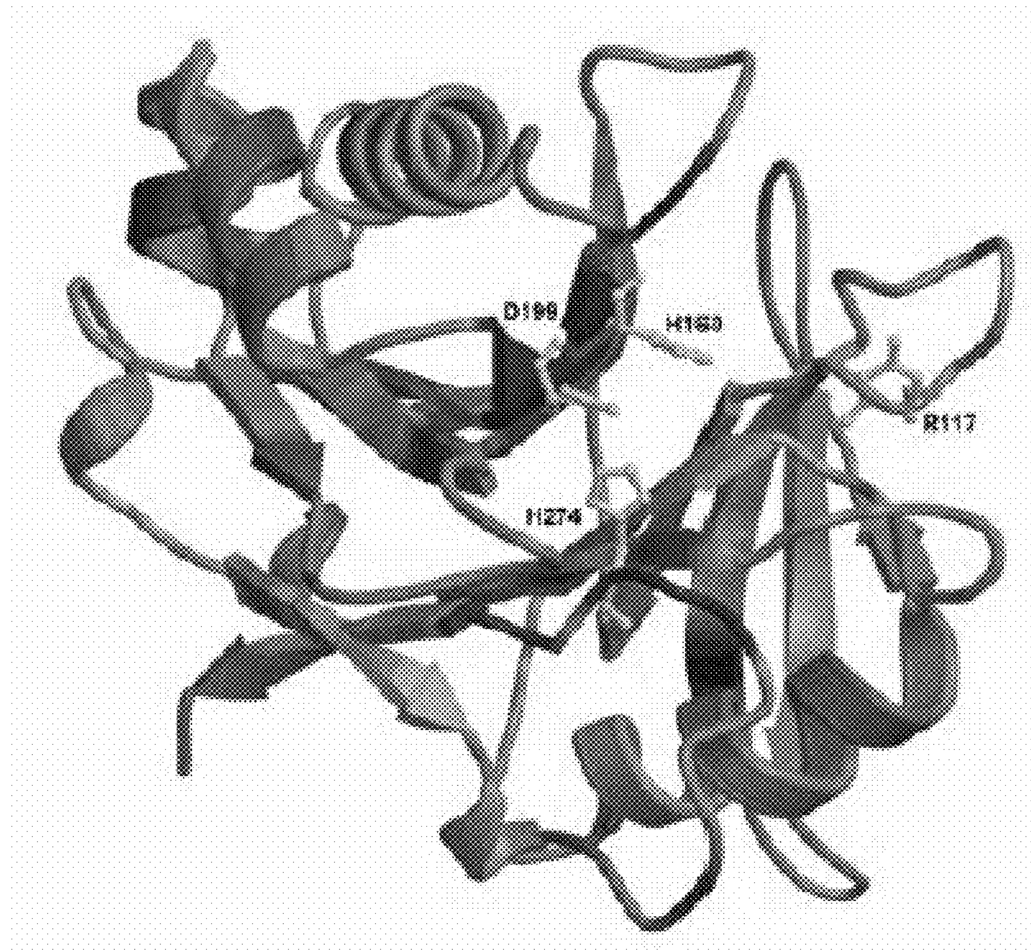
FIG. 5 shows Residue Conservation. A look from above into the active site of CdtB with mutated residues shown in ball-and-stick representation. Individual alignments of CdtB and IP5P homologues were combined and residue conservation was determined for each column of the alignment. Residues that are most conserved between these two groups of proteins are colored in dark gray, with color shading changing towards medium gray (for intermediate conservation) and light gray (lack of conservation). Despite very low pairwise sequence identity between these proteins, the active site shows remarkable degree of conservation that reflects their similar reactions mechanisms.
Figure 6:
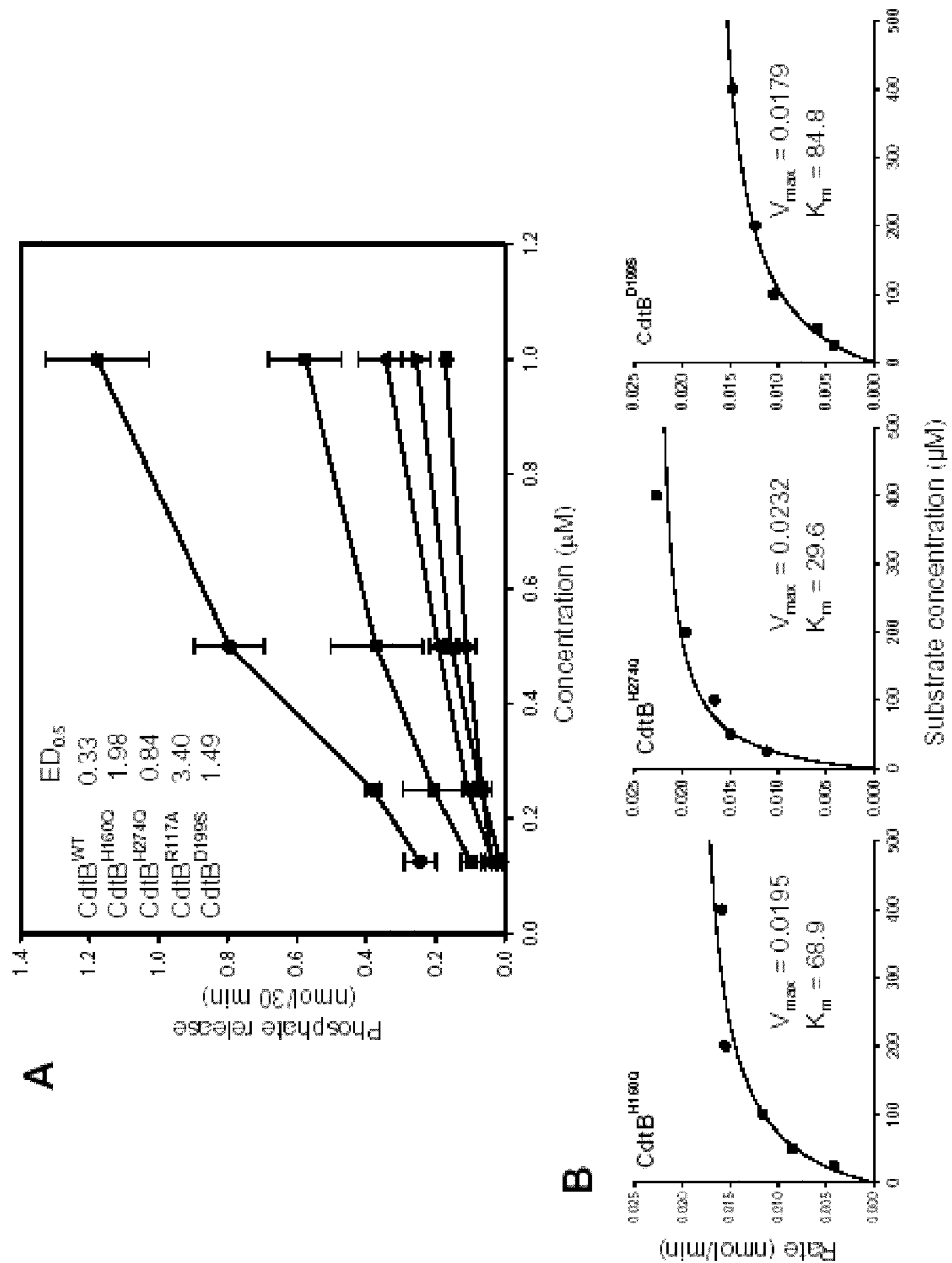
FIG. 6 shows analysis of CdtB mutants for PI-3,4,5-$P_3$ phosphatase activity. Plasmids were constructed containing mutations at residues critical to the putative active site: $CdtB^{H160Q}$, $CdtB^{H274Q}$, $CdtB^{R117A}$ and $CdtB^{D199S}$. The expressed proteins were purified and varying amounts of each were assessed for their ability to hydrolyze PI-3,4,5-$P_3$ (panel A): $CdtB^{WT}$ (circles), $CdtB^{H160Q}$ (downward triangles), $CdtB^{H274Q}$ (squares) $CdtB^{R117A}$ (hexagon) and $CdtB^{D199S}$ (upward triangles). Data are plotted as phosphate release (nmol/30 min; mean±S.D.) versus protein concentration. Panel B shows the rate of phosphate release from PI-3,4,5-$P_3$ was assessed for mutants involving the catalytic site: $CdtB^{H160Q}$, $CdtB^{H274Q}$, and $CdtB^{D99S}$. No analysis was performed on the $CdtB^{R117A}$ mutants because of the low level of activity. Data were analyzed using Michaelis-Menten kinetics; both $K_m$ and $V_{max}$ values are indicated in the respective panels.
Figure 7:
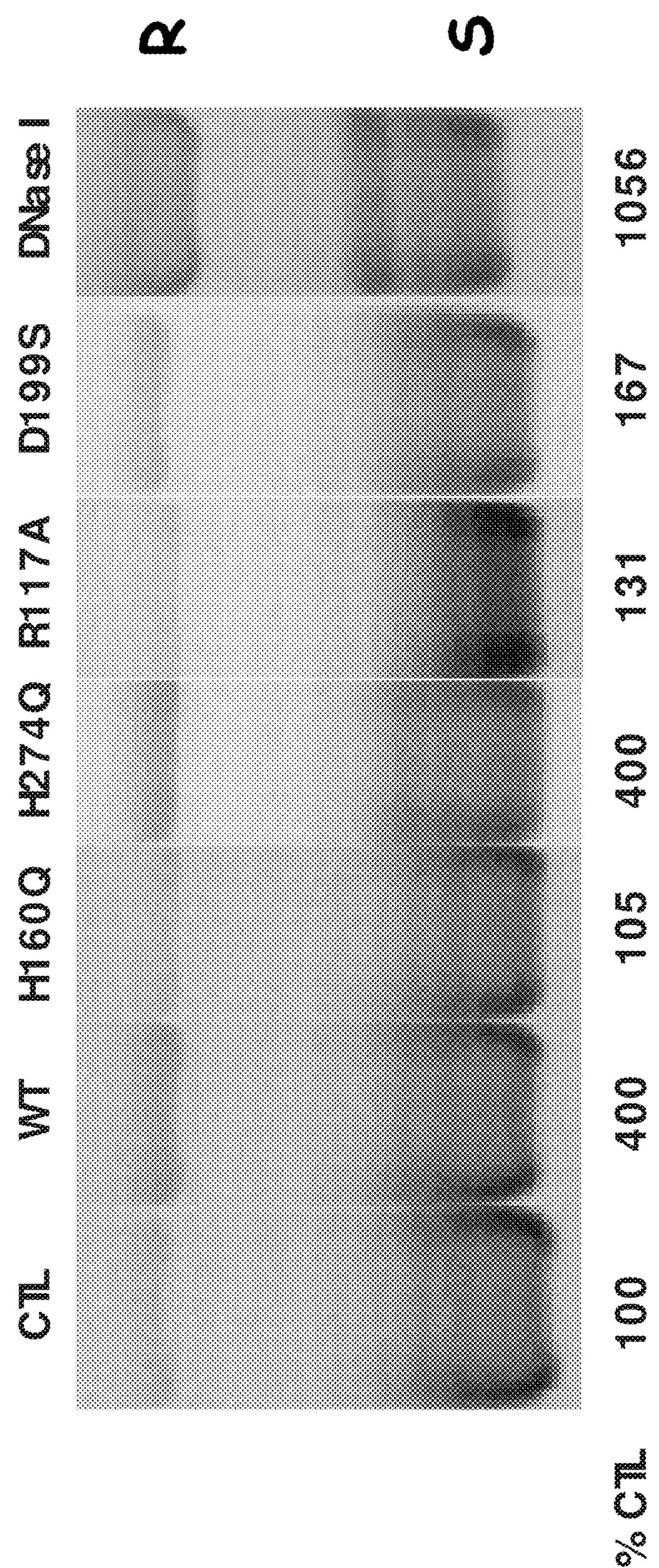
FIG. 7 shows analysis of CdtB mutants for DNase activity. $CdtB^{WT}$ and each of the CdtB mutants (2.5 μg) were incubated with supercoiled pUC19 DNA for 2 hrs at 37° C. as described in Materials and Methods; bovine DNase (1 pg) was employed as a positive control. The samples were then subjected to electrophoresis in agarose gels; after staining with ethidium bromide the gels were analyzed by digital scanning densitometry. S and R refer to supercoiled and relaxed form of plasmid DNA, respectively. Numbers reflect the relative density of the R band expressed as a percentage of the control.

To further explore the relationship between CdtB and inositol polyphosphate 5-phosphatase, several CdtB mutants were generated, which involve amino acid substitutions in residues that correspond to the inositol polyphosphate 5-phosphatase active site and which have previously been shown to be crucial for CdtB toxin activity. FIG. 5 shows a view into the active site of CdtB, with red color corresponding to the best residue conservation estimated from the combined alignment of CdtB and inositol polyphosphate 5-phosphatase homologues. The active site mutations included: $CdtB^{H160Q}$, $CdtB^{H274Q}$, $CdtB^{R117A}$ and $CdtB^{D199S}$; the positions of these residues within the active site are shown in FIG. 5. The mutants were first assessed for their ability to release phosphate from PI-(3,4,5)-$P_3$. As shown in FIG. 6A, each of the mutants was observed to catalyze dose-dependent phosphate release; however, all of the mutants exhibited reduced activity relative to wildtype CdtB ($CdtB^{WT}$); $ED_{0.5}$ values increased from 0.3 μM for $CdtB^{WT}$ to 1.9 ($CdtB^{H160Q}$), 0.8 μM ($CdtB^{H274Q}$), 3.4 (CdtB R17A), and 1.5 μM ($CdtB^{D199S}$). The Michaelis-Menton kinetic parameters were also assessed for these mutations; as shown in FIG. 6B, the $K_m$ values for the mutants was reduced to 68.9 ($CdtB^{H160Q}$), 29.6 ($CdtB^{H274Q}$), and 84.8 ($CdtB^{D199S}$), while the $V_{max}$ was also reduced to 0.019, 0.023 and 0.018 nmoles/min, respectively. Phosphatase activity expressed by $CdtB^{R117A}$ was not sufficient to allow for kinetic analysis. FIG. 7 compares the ability of $CdtB^{WT}$ along with the CdtB mutants to exhibit DNase I-like activity using supercoiled plasmid DNA as a substrate. $CdtB^{WT}$ exhibited detectable nuclease activity although it was less than five orders of magnitude of that observed with bovine DNase I. All of the mutants, with the exception of $CdtB^{H274Q}$, exhibited a reduction in DNase activity; in contrast, $CdtB^{H274Q}$ nuclease activity was comparable to that of $CdtB^{WT}$.

Example 4

CdtB Mutants Exhibit Reduced Capacity for G2 Phase Arrest

Figure 8:
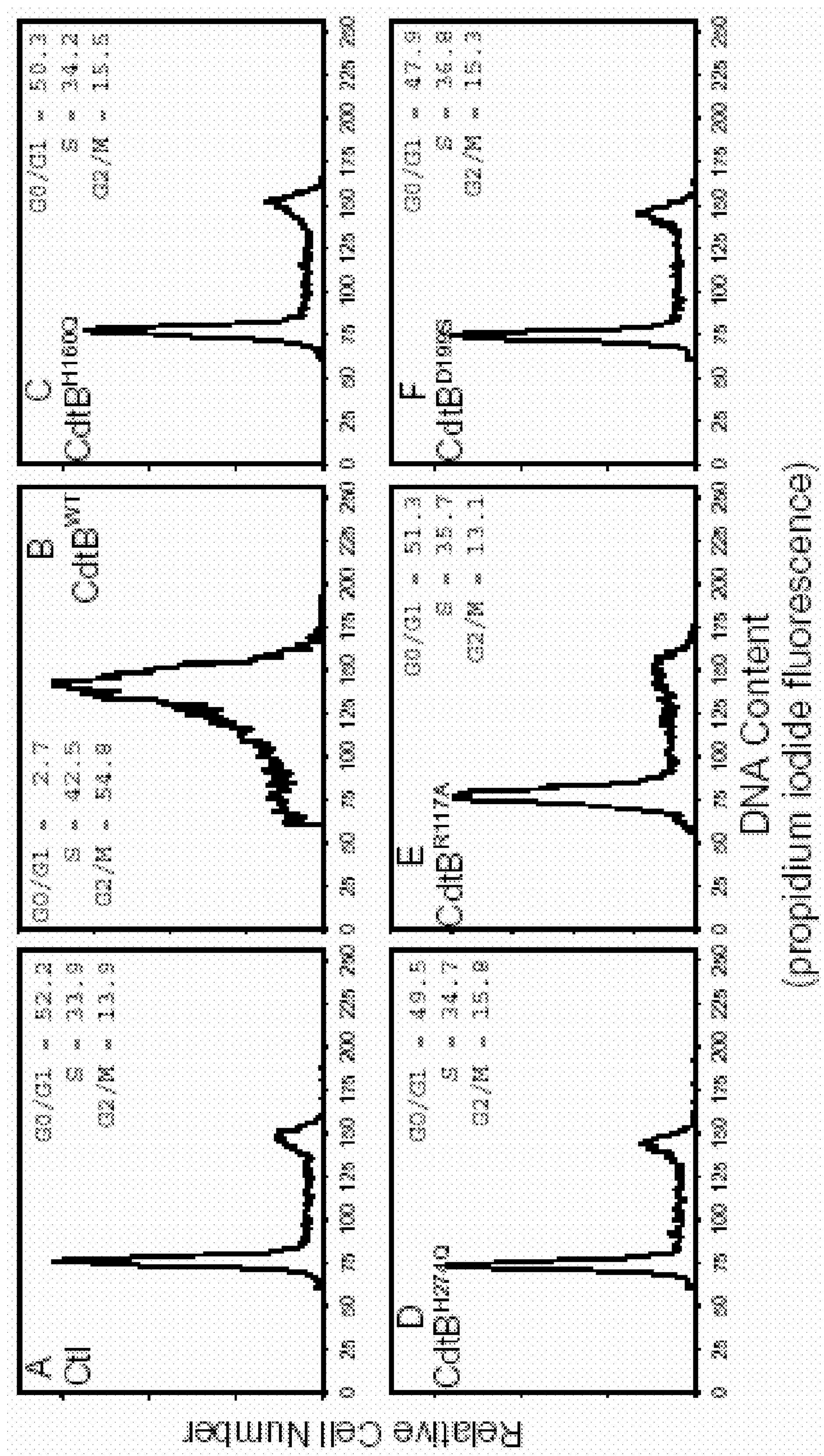
FIG. 8 shows assessment of CdtB mutants for their ability to induce G2 arrest in Jurkat cells. Jurkat cells were exposed to medium alone (panel A) or 10 ng/ml each of CdtA and CdtC in the presence of 4 ng/ml $CdtB^{WT}$ (panel B) or $CdtB^{H160Q}$ (panel C), $CdtB^{H274Q}$ (panel D), $CdtB^{R117A}$ (panel E) or $CdtB^{D199S}$ (panel F). Cells were analyzed for cell cycle distribution 18 hrs after exposure to toxin subunits using flow cytometric analysis of propidium iodide fluorescence (27). The numbers in each panel represent the percentages of cells in G0/G1, S and G2/M. Cells exposed to only 10 ng/ml each of CdtA and CdtC exhibited 14.7% G2 cells (data not shown). Results are representative of three experiments.

The ability of the mutants to induce G2 arrest in Jurkat cells was also assessed. It should be noted that, as previously reported, the ability of CdtB to induce G2 arrest requires the presence of CdtA and CdtC; the combination of individual Cdt subunits produces an active toxin that is not quite as potent (requiring ng of each subunit) as when the three Cdt genes are co-expressed to form a holotoxin. Thus, experiments were done in the presence of CdtA and CdtC under conditions that were previously demonstrated to result in an active toxin complex. As shown in FIG. 8, 13.9% G2 cells were observed in control cultures and 14.7% G2 cells in cultures exposed to only CdtA and CdtC; when 4 ng of $CdtB^{WT}$ was added to CdtA and CdtC, the G2 population increased to 54.8%. In comparison, all of the CdtB mutants lost the ability to induce G2 arrest; the percentage of G2 in these cultures were 15.5% ($CdtB^{H160Q}$), 15.8% ($CdtB^{H274Q}$), 13.1% ($CdtB^{R117A}$) and 15.3% ($CdtB^{D199S}$). It should be noted that the mutants retained residual toxicity if used at higher concentrations (5 μg/ml). These experiments demonstrate a correlation between decreased lipid phosphatase activity and loss of the toxin's ability to induce cell cycle arrest in lymphocytes.

Example 5

Reduction in PI-3,4,5-$P_3$ Synthesis Protects Cells from Cdt-Induced G2 Arrest

Figure 9:
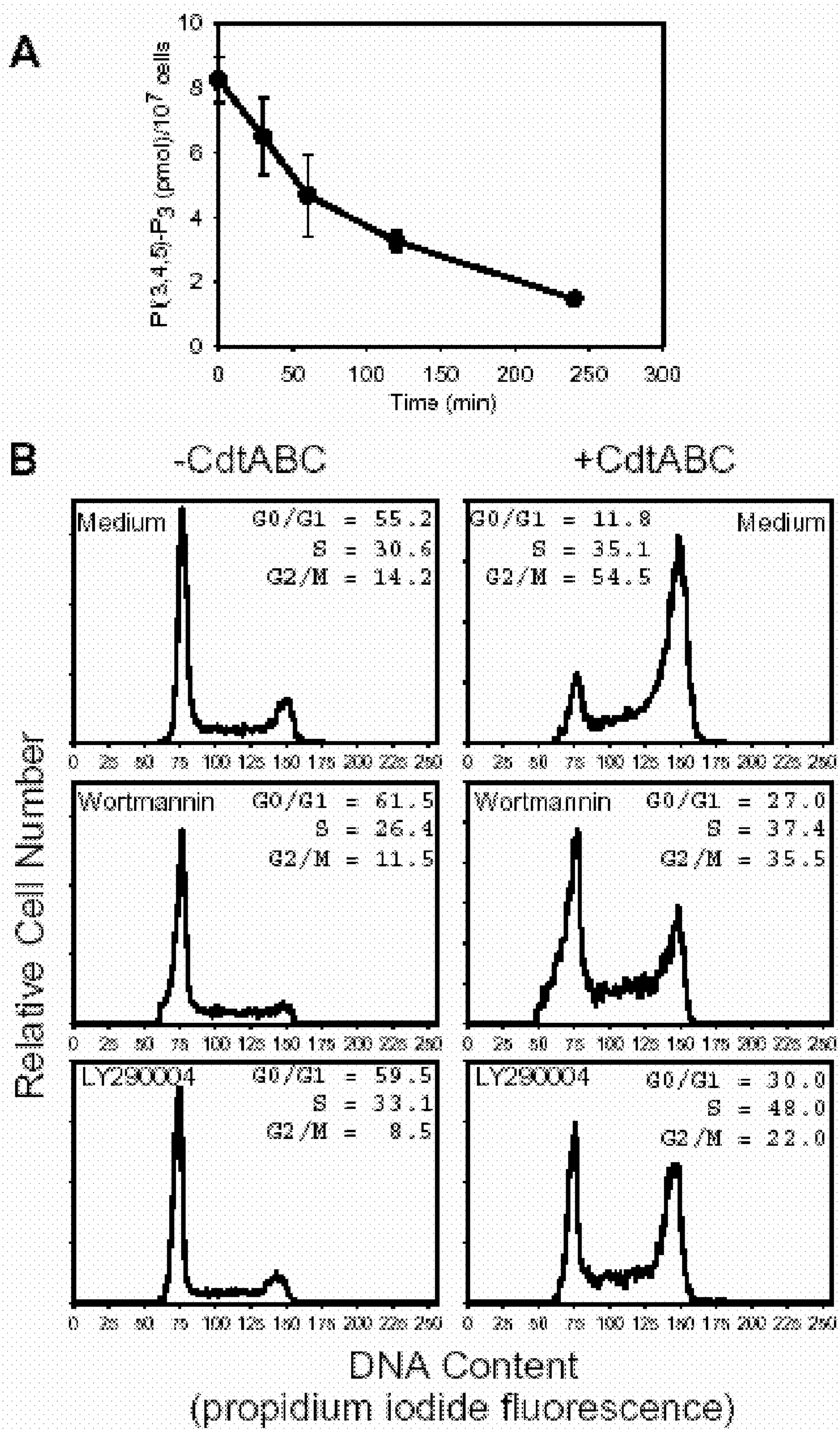
FIG. 9 shows relationship between exposure to Cdt, toxicity and cellular content of PI-3,4,5-$P_3$. (A) Jurkat cells were incubated in the presence of 50 pg/ml CdtABC for varying periods of time. Cells were then harvested, phospholipids extracted and PI-3,4,5-$P_3$ levels determined by ELISA. Data are plotted as PI-3,4,5-$P_3$ content (pmol/$10^7$ cells; mean±S.D.) versus time. (B) PI-3-kinase inhibitors were employed to lower Jurkat cell PI-3,4,5-$P_3$ and thereby alter susceptibility to CdtABC. Jurkat cells were pre-incubated in medium, 250 nM wortmannin or 40 μM LY290004. The cells were then treated with medium or 40 pg/ml CdtABC and assessed for cell cycle distribution by flow cytometry. The numbers in each panel represent the percentages of cells in G0/G1, S and G2/M.

In order to further define the relationship between lipid phosphatase activity and Cdt intoxication of lymphocytes, two lines of investigation were utilized. First, exposure of Jurkat cells to Cdt was demonstrated to result in both a dose and time-dependent reduction of the intracellular levels of PI-3,4,5-$P_3$. As shown in FIG. 9A, treatment of Jurkat cells with a toxic dose of CdtABC (50 μg/ml) results in a time-dependent reduction in PI-3,4,5-$P_3$ levels from 8.3 pmole/$10^7$ cells to 6.5 and 4.7 pmol/$10^7$ cells within 15 and 30 min, respectively; levels were further reduced to 3.3 pmol/$10^7$ cells at 120 min and to 1.5 pmol/$10^7$ cells at 240 min. Cdt treatment also induced a dose-dependent reduction in PI-3,4,5-$P_3$ levels when Jurkat cells were exposed to 50-5000 pg/ml of toxin for 2 hr.

Figure 10:
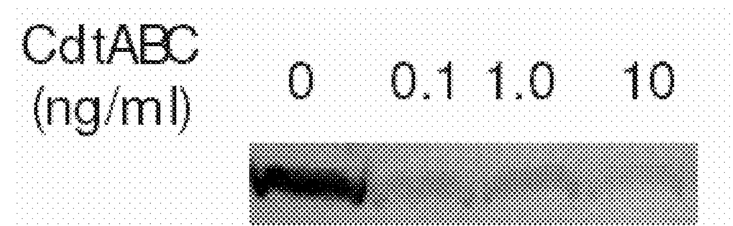
FIG. 10 shows a Western blot analysis of pAKt in Jurkat cells incubated with CdtABC. CdtABC reduces pAKt in Jurkat cells. No differences were observed for Akt.

To examine whether reduced PIP3 correlated with reduced phosphorylated Akt levels, Jurkat cells were treated with varying amounts of CdtABC and then analyzed by Western blot using anti-pAkt specific mAb (FIG. 10). CdtABC caused a dose-dependent reduction in pAkt.

In a second series of experiments, the relationship between lymphocyte susceptibility to toxin and PI-3,4,5-$P_3$ levels were explored. PI-3,4,5-$P_3$ levels in Jurkat cells were first lowered by employing inhibitors of PI-3-kinase. Jurkat cells were pre-treated for 30 min with 250 nM wortmannin or 40 μM LY290004; Cdt holotoxin was added and 16 hr later the cells were assessed for cell cycle distribution. As shown in FIG. 9B, control cells exhibited 14.2% G2 cells while the addition of 40 pg/ml CdtABC increased the percentage of G2 cells to 54.5%. Pre-treatment with either wortmannin or LY290004 reduced Cdt-induced accumulation of G2 cells to 35. % and 22.0%, respectively. Under these conditions, the drugs alone had minimal affect on cell cycle progression. Thus, reducing PI-3,4,5-$P_3$ synthesis protects cells from Cdt-induced G2 arrest.

Example 6

Lymphoid Cell Susceptibility to Cdt-Induced G2 Arrest is Dependent upon the Endogenous Levels of PI-3,4,5-P3

Figure 11:
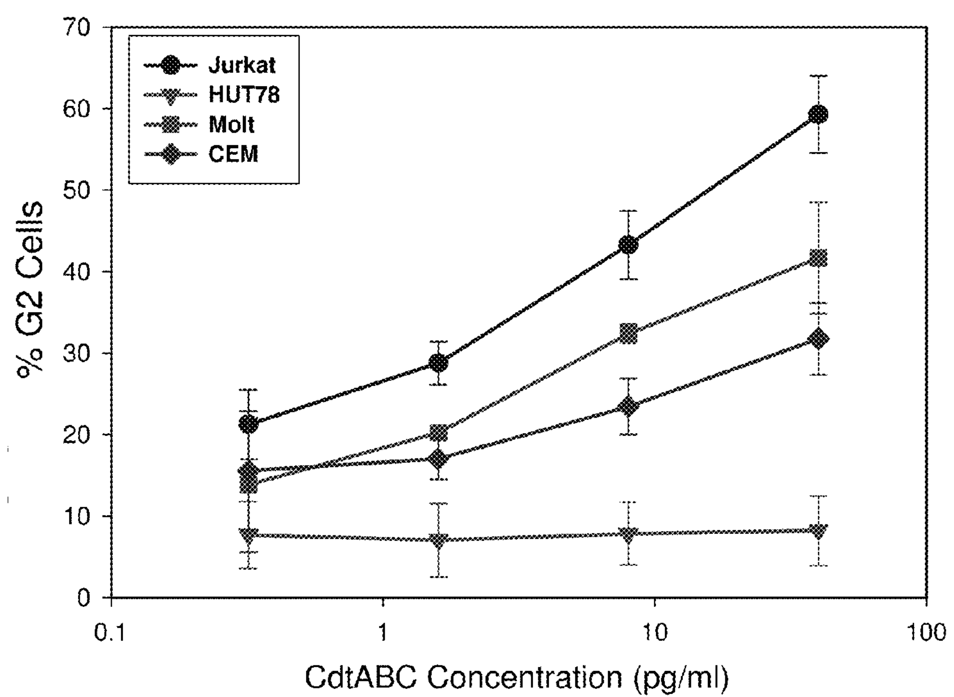
FIG. 11 shows comparison of lymphoid cell line susceptibility to Cdt-induced G2 arrest. Jurkat cells (circles), Hut78 cells (triangles), Molt cells (squares) and CCRF-CEM cells (diamonds) were treated with varying amounts of CdtABC and incubated for 18 hrs. The cells were then harvested, stained with propidium iodine and analyzed by flow cytometry for cell cycle distribution. Data are plotted as percent G2 cells versus CdtABC concentration. Results represent the mean±S.D. of three experiments.

PTEN and SHIP1, both PI-3,4,5-$P_3$ phosphatases, regulate cell proliferation and survival by opposing the action of PI-3-kinase, thereby, maintaining low levels of PI-3,4,5-$P_3$ and blocking activation of Akt. As a consequence of this mode of action, PTEN and SHIP function as tumor suppressors. Indeed, somatic deletions or mutations have been identified in a variety of cancers making them, along with p53, the most commonly mutated genes in human cancers. Of particular relevance, cell lines derived from leukemia and lymphoma patients often exhibit defects in either one or both of these lipid phosphatases. These naturally occurring defects of these phosphatases in lymphoid cell lines were used to assess their relative sensitivity to Cdt. Jurkat cells have been shown to be deficient in both PTEN and SHIP resulting in relatively high levels of PI-3,4,5-$P_3$. As shown in FIG. 11, Jurkat cells exhibit the highest sensitivity to Cdt; the percentage of G2 cells increased from 12.5% in untreated cultures to 21% and 59% in the presence of 0.32 and 40 μg/ml Cdt. In contrast, the cutaneous T-cell lymphoma cell line, Hut78, which contains functional levels of SHIP1 and PTEN as well as low levels of PI-3,4,5-$P_3$ were resistant to the toxin at all concentrations tested. Molt and CEM cells are deficient in PTEN, but have functional SHIP1 activity; these cells exhibit susceptibility to Cdt holotoxin that was less than that observed with Jurkat cells. The percentage of G2 cells increased to 13% (Molt) and 15% (CEM) in the presence of 0.32 μg/ml Cdt and to 41% (Molt) and 32% (CEM) in the presence of 40 μg/ml of toxin. Thus, it appears that lymphoid cell susceptibility to Cdt-induced G2 arrest is dependent upon the endogenous levels of PI-3,4,5-$P_3$ and possibly the cell's dependence on this lipid for proliferation and survival.

Example 7

Figure 12:
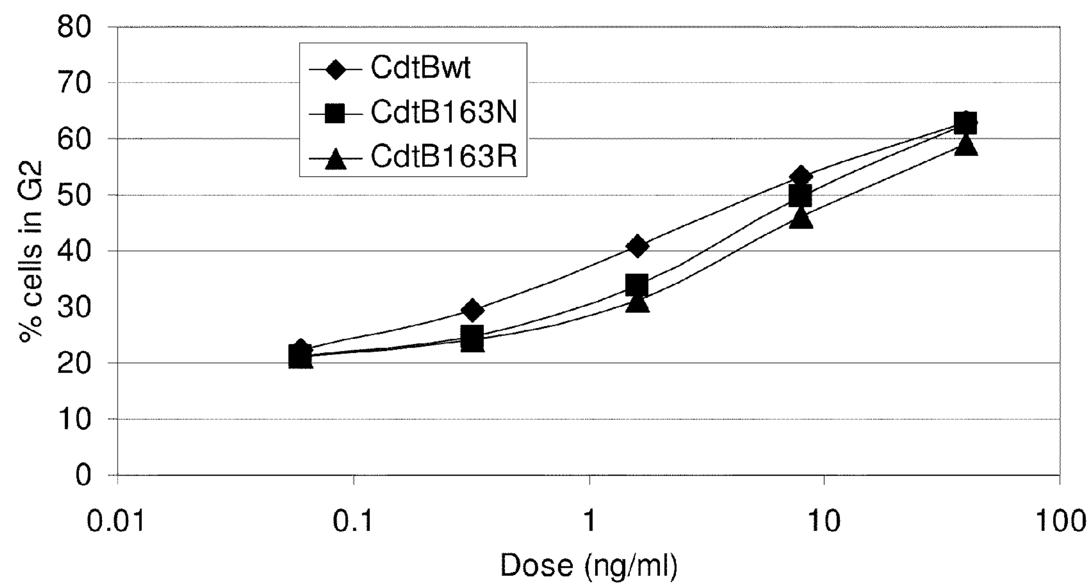
FIG. 12 shows a dose response curve for the ability of $CdtB^{163N}$ and $CdtB^{163R}$ mutants to induce toxicity (G2 cell cycle arrest) in Jurkat cells compared to $CdtB^{wt}$.

$CdtB^{163}$ Mutants Exhibit Reduced DNAse Activity and Comparable Capacity for G2 Phase Arrest CdtB mutants were generated as described hereinabove. Residue 163 of CdtB was targeted because structural analysis suggests that it is a site for substrate binding. FIG. 12 shows a dose response curve for the ability of $CdtB^{wt}$ and $CdtB^{163N}$ and $CdtB^{163R}$ mutants to induce toxicity (G2 cell cycle arrest) in Jurkat cells. Essentially, all three peptides demonstrate comparable activity. Table 2 demonstrates that $CdtB^{A163N}$ and $CdtB^{A163R}$ mutants exhibit phosphatase activity, albeit, slightly reduced from the wildtype. Both $CdtB^{163N}$ and $CdtB^{163R}$ mutants exhibit significantly reduced DNase activity.

TABLE 2

Phosphatase and DNase Activity $CdtB^{wt}$ and mutants

| | PIP3 phosphatase activity (% $CdtB^{wt}$) | DNase Activity (% $CdtB^{wt}$) |
|---|---|---|
| $CdtB^{wt}$ | 100 | 100 |
| $CdtB^{163N}$ | 65 | 5 |
| $CdtB^{163R}$ | 68 | <1 |

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for inhibiting the proliferation of a lymphocyte cell the method comprising: contacting said cell with a CdtB toxin comprising the amino acid sequence as set forth in SEQ ID NO:3 having a mutation at amino acid position 163 of the CdtB toxin, thereby inhibiting the proliferation of said lymphocyte cell at its G2 phase.

2. The method of claim 1, wherein said mutation is A163N or A163R.

3. The method of claim 1, wherein said method further comprising contacting said cell with an agent capable of reducing the concentration of PI-3,4,5-triphosphate.

4. The method of claim 1, wherein said CdtB toxin is derived from *Actinobacillus actinomycetemcomitans*.

* * * * *

SEQUENCE LISTING

<160> NUMBER OF SEQ ID NOS: 22

<210> SEQ ID NO 1
<211> LENGTH: 163
<212> TYPE: PRT
<213> ORGANISM: Actinobacillus actinomycetemcomitans

<400> SEQUENCE: 1

Leu Leu Ser Ser Ser Lys Asn Gly Gln Val Ser Pro Ser Glu Pro Ser
1               5                   10                  15

Asn Phe Met Thr Leu Met Gly Gln Asn Gly Ala Leu Leu Thr Val Trp
            20                  25                  30

Ala Leu Ala Lys Arg Asn Trp Leu Trp Ala Tyr Pro Asn Ile Tyr Ser
        35                  40                  45

Gln Asp Phe Gly Asn Ile Arg Asn Trp Lys Ile Glu Pro Gly Lys His
    50                  55                  60

Arg Glu Tyr Phe Arg Phe Val Asn Gln Ser Leu Gly Thr Cys Ile Glu
65                  70                  75                  80

Ala Tyr Gly Asn Gly Leu Ile His Asp Thr Cys Ser Leu Asp Lys Leu
                85                  90                  95

Ala Gln Glu Phe Glu Leu Leu Pro Thr Asp Ser Gly Ala Val Val Ile
            100                 105                 110

Lys Ser Val Ser Gln Gly Arg Cys Val Thr Tyr Asn Pro Val Ser Pro
        115                 120                 125

Thr Tyr Tyr Ser Thr Val Thr Leu Ser Thr Cys Asp Gly Ala Thr Glu
    130                 135                 140

Pro Leu Arg Asp Gln Thr Trp Tyr Leu Ala Pro Pro Val Leu Glu Ala
145                 150                 155                 160

Thr Ala Val

<210> SEQ ID NO 2
<211> LENGTH: 489
<212> TYPE: DNA
<213> ORGANISM: Actinobacillus actinomycetemcomitans

<400> SEQUENCE: 2
ttgctctctt catccaagaa tggacaggta tcgccgtctg aaccatcaaa ctttatgact     60
ttgatgggac aaaatggggc actgttgact gtctgggcgc tagcaaaacg caattggtta    120
tgggcttatc ccaatatata ttcgcaggac tttggaaata ttcgtaattg gaagatagaa    180
cctggtaaac accgtgaata ttttcgtttt gttaatcaat ctttaggtac atgtattgaa    240
gcttacggta atggtttaat tcatgatact tgtagtctgg acaaattagc acaagagttt    300
gagttattac ctactgatag tggtgcggtt gtcattaaaa gtgtgtcaca aggacgttgt    360
gtcacttata atcctgtaag tccaacatat tattcaacag ttacattatc aacttgtgat    420
ggcgcaacag aaccattacg tgatcaaaca tggtatctcg ctcctcctgt attagaagca    480
acagcggtt                                                            489

<210> SEQ ID NO 3
<211> LENGTH: 261
<212> TYPE: PRT
<213> ORGANISM: Actinobacillus actinomycetemcomitans

<400> SEQUENCE: 3

Asn Leu Ser Asp Phe Lys Val Ala Thr Trp Asn Leu Gln Gly Ser Ser
1               5                   10                  15

```
Ala Val Asn Glu Ser Lys Trp Asn Ile Asn Val Arg Gln Leu Leu Ser
            20                  25                  30

Gly Glu Gln Gly Ala Asp Ile Leu Met Val Gln Glu Ala Gly Ser Leu
        35                  40                  45

Pro Ser Ser Ala Val Arg Thr Ser Arg Val Ile Gln His Gly Gly Thr
    50                  55                  60

Pro Ile Glu Glu Tyr Thr Trp Asn Leu Gly Thr Arg Ser Arg Pro Asn
65                  70                  75                  80

Met Val Tyr Ile Tyr Tyr Ser Arg Leu Asp Val Gly Ala Asn Arg Val
                85                  90                  95

Asn Leu Ala Ile Val Ser Arg Arg Gln Ala Asp Glu Ala Phe Ile Val
            100                 105                 110

His Ser Asp Ser Ser Val Leu Gln Ser Arg Pro Ala Val Gly Ile Arg
        115                 120                 125

Ile Gly Thr Asp Val Phe Phe Thr Val His Ala Leu Ala Thr Gly Gly
    130                 135                 140

Ser Asp Ala Val Ser Leu Ile Arg Asn Ile Phe Thr Thr Phe Thr Ser
145                 150                 155                 160

Ser Pro Ser Ser Pro Glu Arg Arg Gly Tyr Ser Trp Met Val Val Gly
                165                 170                 175

Asp Phe Asn Arg Ala Pro Val Asn Leu Glu Ala Ala Leu Arg Gln Glu
            180                 185                 190

Pro Ala Val Ser Glu Asn Thr Ile Ile Ile Ala Pro Thr Glu Pro Thr
        195                 200                 205

His Arg Ser Gly Asn Ile Leu Asp Tyr Ala Ile Leu His Asp Ala His
    210                 215                 220

Leu Pro Arg Arg Glu Gln Ala Arg Glu Arg Ile Gly Ala Ser Leu Met
225                 230                 235                 240

Leu Asn Gln Leu Arg Ser Gln Ile Thr Ser Asp His Phe Pro Val Ser
                245                 250                 255

Phe Val Arg Asp Arg
            260


<210> SEQ ID NO 4
<211> LENGTH: 781
<212> TYPE: DNA
<213> ORGANISM: Actinobacillus actinomycetemcomitans

<400> SEQUENCE: 4

aacttgagtg atttcaaagt agcaacttgg aatctgcaag gttcttcagc tgtaaatgaa      60

agtaaatgga atattaatgt gcgccaatta ttatcgggag aacaaggtgc agatattttg     120

atggtacaag aagcgggttc attaccaagt tcggcagtaa gaacctcacg agtaattcaa     180

catgggggaa cgccaattga ggaatatacc tggaatttag gtactcgctc ccgtccaaat     240

atggtctata tttattattc ccgtttagat gttggggcaa accgagtgaa cttagctatc     300

gtgtcacgtc gtcaagccga tgaagctttt atcgtacatt ctgattcttc tgtgcttcaa     360

tctcgcccgg cagtaggtat ccgcattggt actgatgtat tttttacagt gcatgctttg     420

gccacaggtg gttctgatgc ggtaagttta attcgtaata tcttcactac ttttacctca     480

tcaccatcat caccggaaag acgaggatat agctggatgg ttgttggtga tttcaatcgt     540

gcgccggtta atctggaagc tgcattaaga caggaacccg ccgtgagtga aaatacaatt     600

attattgcgc caacagaacc gactcatcgg tccggtaata ttttagatta tgcgatttta     660

catgacgcac atttaccacg tcgagagcaa gcacgtgaac gtatcggcgc aagtttaatg     720
```

```
ttaaatcagt tacgctcaca aattacatcc gatcattttc ctgttagttt tgttcgtgat    780

c                                                                    781


<210> SEQ ID NO 5
<211> LENGTH: 166
<212> TYPE: PRT
<213> ORGANISM: Actinobacillus actinomycetemcomitans

<400> SEQUENCE: 5

Glu Ser Asn Pro Asp Pro Thr Thr Tyr Pro Asp Val Glu Leu Ser Pro
1               5                   10                  15

Pro Pro Arg Ile Ser Leu Arg Ser Leu Leu Thr Ala Gln Pro Ile Lys
            20                  25                  30

Asn Asp His Tyr Asp Ser His Asn Tyr Leu Ser Thr His Trp Glu Leu
        35                  40                  45

Ile Asp Tyr Lys Gly Lys Glu Tyr Glu Lys Leu Arg Asp Gly Gly Thr
    50                  55                  60

Leu Val Gln Phe Lys Val Val Gly Ala Ala Lys Cys Phe Ala Phe Pro
65                  70                  75                  80

Gly Glu Gly Thr Thr Asp Cys Lys Asp Ile Asp His Thr Val Phe Asn
                85                  90                  95

Leu Ile Pro Thr Asn Thr Gly Ala Phe Leu Ile Lys Asp Ala Leu Leu
            100                 105                 110

Gly Phe Cys Met Thr Ser His Asp Phe Asp Asp Leu Arg Leu Glu Pro
        115                 120                 125

Cys Gly Ile Ser Val Ser Gly Arg Thr Phe Ser Leu Ala Tyr Gln Trp
    130                 135                 140

Gly Ile Leu Pro Pro Phe Gly Pro Ser Lys Ile Leu Arg Pro Pro Val
145                 150                 155                 160

Gly Arg Asn Gln Gly Ser
                165


<210> SEQ ID NO 6
<211> LENGTH: 498
<212> TYPE: DNA
<213> ORGANISM: Actinobacillus actinomycetemcomitans

<400> SEQUENCE: 6

gaatcaaatc ctgatccgac tacttatcct gatgtagagt tatcgcctcc tccacgtatt     60

agcttgcgta gtttgcttac ggctcaacca attaaaaatg accattatga ttcacataat    120

tatttaagta cacattggga attaattgat tacaagggaa aagaatatga aaaattacgt    180

gacggtggta cgttggttca atttaaagtg gtcggtgcag caaaatgttt tgctttccca    240

ggcgaaggca caactgattg taaagatatt gatcatactg tgtttaacct tattccaact    300

aatacaggtg cgtttttaat caaagatgcc ctattaggat tttgtatgac aagccatgac    360

tttgatgatt tgaggcttga accttgtgga atttcagtga gtggtcgaac cttttcgttg    420

gcgtatcaat ggggaatatt acctcctttt gggccaagta aaattttaag accaccggtg    480

gggagaaatc agggtagc                                                  498


<210> SEQ ID NO 7
<211> LENGTH: 185
<212> TYPE: PRT
<213> ORGANISM: Artificial Sequence
<220> FEATURE:
<223> OTHER INFORMATION: Structural alignment of CdtB with inositol
      polyphosphate 5-phosphatase (IP5P) and DNase I
```

<400> SEQUENCE: 7

```
Asn Leu Ser Asp Phe Lys Val Ala Thr Trp Asn Leu Gln Gly Ser Ser
1               5                   10                  15

Ala Val Asn Glu Ser Lys Trp Asn Ile Asn Gly Ala Asp Ile Leu Met
            20                  25                  30

Val Gln Glu Ala Gly Ser Pro Asn Met Val Tyr Ile Tyr Tyr Ser Arg
        35                  40                  45

Arg Val Asn Leu Ala Ile Val Ser Arg Arg Gln Ala Asp Glu Ala Phe
    50                  55                  60

Ile Val His Ser Asp Arg Pro Ala Val Gly Ile Arg Ile Gly Thr Asp
65                  70                  75                  80

Val Phe Phe Thr Val His Ala Leu Ala Thr Gly Gly Ser Asp Ala Val
                85                  90                  95

Ser Leu Ile Arg Asn Ile Phe Thr Thr Phe Arg Gly Tyr Ser Trp Met
            100                 105                 110

Val Val Gly Asp Phe Asn Arg Ala Pro Val Asn Leu Glu Ala Ala Leu
        115                 120                 125

Arg Gln Glu Pro Ala Val Ser Glu Asn Thr Ile Ile Ile Ala Pro Thr
    130                 135                 140

Glu Pro Thr His Gln Ser Gly Asn Ile Leu Asp Tyr Ala Ile Leu His
145                 150                 155                 160

Asp Ala His Leu Arg Ile Gly Ala Ser Leu Met Ile Thr Ser Asp His
                165                 170                 175

Phe Pro Val Ser Phe Val His Asp Arg
            180                 185
```

<210> SEQ ID NO 8
<211> LENGTH: 178
<212> TYPE: PRT
<213> ORGANISM: Artificial Sequence
<220> FEATURE:
<223> OTHER INFORMATION: Structural alignment of inositol polyphosphate 5-phosphatase (IP5P) with CdtB and DNase I

<400> SEQUENCE: 8

```
Ile Phe Val Ala Ser Tyr Asn Leu Asn Gly Cys Ser Ala Thr Thr Lys
1               5                   10                  15

Leu Glu Asn Trp Leu Phe Pro Asp Ile Tyr Val Val Gly Phe Gln Glu
            20                  25                  30

Ile Val Gln Pro Gly Tyr Val Gln Leu Arg Ser Gly Gln Leu Val Gly
        35                  40                  45

Thr Ala Leu Met Ile Phe Val Glu Gly Thr Val Lys Lys Thr Gly Ala
    50                  55                  60

Val Ala Ile Arg Phe Asp Tyr Glu Asp Thr Gly Leu Cys Phe Ile Thr
65                  70                  75                  80

Ser His Leu Ala Ala Gly Tyr Thr Asn Tyr Asp Glu Arg Asp His Asp
                85                  90                  95

Tyr Arg Thr Ile Ala Ser Gly Leu Asn His Asp Tyr Val Val Trp Phe
            100                 105                 110

Gly Asp Phe Asn Tyr Arg Asp Gln Leu Asn Lys Gln Met Leu Thr Gly
        115                 120                 125

Lys Val Phe Pro Phe Phe Ser Glu Leu Pro Ile Thr Phe Pro Arg Val
    130                 135                 140

Pro Ala Trp Thr Asp Arg Ile Leu Tyr Arg Gly Glu Leu Val Ser Tyr
145                 150                 155                 160
```

```
Gln Ser Val Pro Leu Tyr Tyr Ser Asp His Arg Pro Ile Tyr Ala Thr
                165                 170                 175

Tyr Glu
```

<210> SEQ ID NO 9
<211> LENGTH: 186
<212> TYPE: PRT
<213> ORGANISM: Artificial Sequence
<220> FEATURE:
<223> OTHER INFORMATION: Structural alignment of DNase I with CdtB and inositol polyphosphate 5-phosphatase (IP5P)

<400> SEQUENCE: 9

```
Leu Lys Ile Ala Ala Phe Asn Ile Arg Thr Phe Gly Glu Thr Leu Ala
1               5                   10                  15

Ser Tyr Ile Val Arg Ile Arg Tyr Asp Ile Val Leu Ile Gln Glu Val
            20                  25                  30

Arg Asp Asn Thr Tyr His Tyr Val Val Ser Glu Pro Lys Glu Arg Tyr
        35                  40                  45

Leu Phe Leu Phe Arg Val Leu Asp Thr Tyr Gln Tyr Asp Asp Asp Ser
    50                  55                  60

Phe Ser Arg Glu Pro Ala Val Val Lys Phe Ser Glu Phe Ala Ile Val
65                  70                  75                  80

Ala Leu His Ser Ala Pro Ser Asp Ala Val Ala Glu Ile Asn Ser Leu
                85                  90                  95

Tyr Asp Val Tyr Leu Asp Val His Leu Asn Asp Val Met Leu Met Gly
            100                 105                 110

Asp Phe Asn Ala Asp Cys Ser Tyr Val Thr Ser Ser Gln Trp Ser Ser
        115                 120                 125

Ile Arg Leu Arg Thr Ser Ser Thr Phe Gln Trp Leu Ile Pro Asp Ser
    130                 135                 140

Ala Asp Thr Thr Ala Thr Ser Thr Asn Cys Ala Tyr Asp Arg Ile Val
145                 150                 155                 160

Val Ala Gly Ser Leu Leu Pro Gly Ser Ala Ala Pro Phe Ala Ile Ser
                165                 170                 175

Asp His Tyr Pro Val Glu Val Thr Leu Thr
            180                 185
```

<210> SEQ ID NO 10
<211> LENGTH: 100
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(100)
<223> OTHER INFORMATION: small (s), aliphatic (l), hydrophobic (h), charged (c), positive (+) and negative (-) residues
<220> FEATURE:
<221> NAME/KEY: MISC_FEATURE
<222> LOCATION: (1)..(1)
<223> OTHER INFORMATION: hydrophobic
<220> FEATURE:
<221> NAME/KEY: MISC_FEATURE
<222> LOCATION: (2)..(2)
<223> OTHER INFORMATION: aliphatic residue
<220> FEATURE:
<221> NAME/KEY: MISC_FEATURE
<222> LOCATION: (4)..(4)
<223> OTHER INFORMATION: small residue
<220> FEATURE:
<221> NAME/KEY: MISC_FEATURE
<222> LOCATION: (5)..(5)
<223> OTHER INFORMATION: aliphatic residue
<220> FEATURE:
<221> NAME/KEY: MISC_FEATURE
<222> LOCATION: (7)..(7)
<223> OTHER INFORMATION: aliphatic residue
<220> FEATURE:
<221> NAME/KEY: MISC_FEATURE
<222> LOCATION: (8)..(10)
<223> OTHER INFORMATION: small residues
<220> FEATURE:
<221> NAME/KEY: MISC_FEATURE
<222> LOCATION: (11)..(12)
<223> OTHER INFORMATION: hydrophobic residues
<220> FEATURE:
<221> NAME/KEY: MISC_FEATURE
<222> LOCATION: (13)..(14)
<223> OTHER INFORMATION: aliphatic residues
<220> FEATURE:
<221> NAME/KEY: MISC_FEATURE
<222> LOCATION: (15)..(16)
<223> OTHER INFORMATION: hydrophobic residues
<220> FEATURE:
<221> NAME/KEY: MISC_FEATURE
<222> LOCATION: (19)..(19)
<223> OTHER INFORMATION: hydrophobic residue
<220> FEATURE:
<221> NAME/KEY: MISC_FEATURE
<222> LOCATION: (20)..(21)
<223> OTHER INFORMATION: small residues
<220> FEATURE:
<221> NAME/KEY: MISC_FEATURE
<222> LOCATION: (22)..(23)
<223> OTHER INFORMATION: hydrophobic residues
<220> FEATURE:
<221> NAME/KEY: MISC_FEATURE
<222> LOCATION: (24)..(24)
<223> OTHER INFORMATION: aliphatic residue
<220> FEATURE:
<221> NAME/KEY: MISC_FEATURE
<222> LOCATION: (25)..(28)
<223> OTHER INFORMATION: hydrophobic residues
<220> FEATURE:
<221> NAME/KEY: MISC_FEATURE
<222> LOCATION: (29)..(29)
<223> OTHER INFORMATION: negative residue
<220> FEATURE:
<221> NAME/KEY: MISC_FEATURE
<222> LOCATION: (30)..(30)
<223> OTHER INFORMATION: small residue
<220> FEATURE:
<221> NAME/KEY: MISC_FEATURE
<222> LOCATION: (31)..(31)
<223> OTHER INFORMATION: hydrophobic residue
<220> FEATURE:
<221> NAME/KEY: MISC_FEATURE
<222> LOCATION: (32)..(32)
<223> OTHER INFORMATION: charged residue
<220> FEATURE:
<221> NAME/KEY: MISC_FEATURE
<222> LOCATION: (33)..(35)
<223> OTHER INFORMATION: small residues
<220> FEATURE:
<221> NAME/KEY: MISC_FEATURE
<222> LOCATION: (36)..(37)
<223> OTHER INFORMATION: hydrophobic residues
<220> FEATURE:
<221> NAME/KEY: MISC_FEATURE
<222> LOCATION: (38)..(38)
<223> OTHER INFORMATION: charged residue
<220> FEATURE:
<221> NAME/KEY: MISC_FEATURE
<222> LOCATION: (39)..(39)
<223> OTHER INFORMATION: hydrophobic residue
<220> FEATURE:
<221> NAME/KEY: MISC_FEATURE
<222> LOCATION: (40)..(40)
<223> OTHER INFORMATION: small residue
<220> FEATURE:
<221> NAME/KEY: MISC_FEATURE
<222> LOCATION: (41)..(42)
<223> OTHER INFORMATION: hydrophobic residues
<220> FEATURE:
<221> NAME/KEY: MISC_FEATURE
<222> LOCATION: (43)..(43)
<223> OTHER INFORMATION: small residue
<220> FEATURE:
<221> NAME/KEY: MISC_FEATURE
<222> LOCATION: (45)..(45)
<223> OTHER INFORMATION: hydrophobic residue
<220> FEATURE:
<221> NAME/KEY: MISC_FEATURE
<222> LOCATION: (46)..(47)
<223> OTHER INFORMATION: small residues
<220> FEATURE:
<221> NAME/KEY: MISC_FEATURE
<222> LOCATION: (48)..(48)
<223> OTHER INFORMATION: hydrophobic residue
<220> FEATURE:
<221> NAME/KEY: MISC_FEATURE
<222> LOCATION: (49)..(49)
<223> OTHER INFORMATION: small residue
<220> FEATURE:
<221> NAME/KEY: MISC_FEATURE
<222> LOCATION: (50)..(50)
<223> OTHER INFORMATION: hydrophobic residue
<220> FEATURE:
<221> NAME/KEY: MISC_FEATURE
<222> LOCATION: (51)..(51)
<223> OTHER INFORMATION: small residue
<220> FEATURE:
<221> NAME/KEY: MISC_FEATURE
<222> LOCATION: (52)..(52)
<223> OTHER INFORMATION: aliphatic residue
<220> FEATURE:
<221> NAME/KEY: MISC_FEATURE
<222> LOCATION: (53)..(53)
<223> OTHER INFORMATION: hydrophobic residue
<220> FEATURE:
<221> NAME/KEY: MISC_FEATURE
<222> LOCATION: (54)..(54)
<223> OTHER INFORMATION: small residue
<220> FEATURE:
<221> NAME/KEY: MISC_FEATURE
<222> LOCATION: (55)..(60)
<223> OTHER INFORMATION: hydrophobic residues
<220> FEATURE:
<221> NAME/KEY: MISC_FEATURE
<222> LOCATION: (65)..(65)
<223> OTHER INFORMATION: small residue
<220> FEATURE:
<221> NAME/KEY: MISC_FEATURE
<222> LOCATION: (66)..(68)
<223> OTHER INFORMATION: hydrophobic residues
<220> FEATURE:
<221> NAME/KEY: MISC_FEATURE
<222> LOCATION: (69)..(69)
<223> OTHER INFORMATION: small residue
<220> FEATURE:
<221> NAME/KEY: MISC_FEATURE
<222> LOCATION: (70)..(71)
<223> OTHER INFORMATION: hydrophobic residues
<220> FEATURE:
<221> NAME/KEY: MISC_FEATURE
<222> LOCATION: (72)..(73)
<223> OTHER INFORMATION: small residues
<220> FEATURE:
<221> NAME/KEY: MISC_FEATURE
<222> LOCATION: (74)..(74)
<223> OTHER INFORMATION: hydrophobic residue
<220> FEATURE:
<221> NAME/KEY: MISC_FEATURE
<222> LOCATION: (75)..(77)
<223> OTHER INFORMATION: small residues
<220> FEATURE:
<221> NAME/KEY: MISC_FEATURE
<222> LOCATION: (78)..(79)
<223> OTHER INFORMATION: hydrophobic residues
<220> FEATURE:
<221> NAME/KEY: MISC_FEATURE
<222> LOCATION: (81)..(81)
<223> OTHER INFORMATION: hydrophobic residue

```
<220> FEATURE:
<221> NAME/KEY: MISC_FEATURE
<222> LOCATION: (82)..(82)
<223> OTHER INFORMATION: aliphatic residue
<220> FEATURE:
<221> NAME/KEY: MISC_FEATURE
<222> LOCATION: (83)..(83)
<223> OTHER INFORMATION: hydrophobic residue
<220> FEATURE:
<221> NAME/KEY: MISC_FEATURE
<222> LOCATION: (84)..(84)
<223> OTHER INFORMATION: small residue
<220> FEATURE:
<221> NAME/KEY: MISC_FEATURE
<222> LOCATION: (85)..(85)
<223> OTHER INFORMATION: hydrophobic residue
<220> FEATURE:
<221> NAME/KEY: MISC_FEATURE
<222> LOCATION: (87)..(87)
<223> OTHER INFORMATION: hydrophobic residue
<220> FEATURE:
<221> NAME/KEY: MISC_FEATURE
<222> LOCATION: (88)..(89)
<223> OTHER INFORMATION: small residues
<220> FEATURE:
<221> NAME/KEY: MISC_FEATURE
<222> LOCATION: (90)..(92)
<223> OTHER INFORMATION: hydrophobic residues
<220> FEATURE:
<221> NAME/KEY: MISC_FEATURE
<222> LOCATION: (97)..(97)
<223> OTHER INFORMATION: aliphatic residue
<220> FEATURE:
<221> NAME/KEY: MISC_FEATURE
<222> LOCATION: (98)..(98)
<223> OTHER INFORMATION: hydrophobic residue
<220> FEATURE:
<221> NAME/KEY: MISC_FEATURE
<222> LOCATION: (99)..(99)
<223> OTHER INFORMATION: small residue
<220> FEATURE:
<221> NAME/KEY: MISC_FEATURE
<222> LOCATION: (100)..(100)
<223> OTHER INFORMATION: hydrophobic residue

<400> SEQUENCE: 10

Xaa Xaa Ala Xaa Xaa Asn Xaa Xaa Xaa Xaa Xaa Xaa Xaa Xaa Xaa Xaa
1               5                   10                  15

Gln Glu Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa His Xaa Xaa Xaa Xaa
        35                  40                  45

Xaa Xaa Xaa Xaa Xaa Xaa Xaa Xaa Xaa Xaa Xaa Xaa Gly Asp Phe Asn
    50                  55                  60

Xaa Xaa Xaa Xaa Xaa Xaa Xaa Xaa Xaa Xaa Xaa Xaa Xaa Xaa Xaa Asp
65                  70                  75                  80

Xaa Xaa Xaa Xaa Xaa Xaa Xaa Xaa Xaa Xaa Xaa Xaa Ser Asp His Pro
                85                  90                  95

Xaa Xaa Xaa Xaa
            100


<210> SEQ ID NO 11
<211> LENGTH: 30
<212> TYPE: DNA
<213> ORGANISM: Artificial Sequence
<220> FEATURE:
<223> OTHER INFORMATION: pGEMCdtBH160Q Primer 1

<400> SEQUENCE: 11

gtatttttta cagtgcaggc tttggccaca                                      30
```

<210> SEQ ID NO 12
<211> LENGTH: 30
<212> TYPE: DNA
<213> ORGANISM: Artificial Sequence
<220> FEATURE:
<223> OTHER INFORMATION: pGEMCdtBH160Q Primer 2

<400> SEQUENCE: 12
tgtggccaaa gcctgcactg taaaaaatac 30

<210> SEQ ID NO 13
<211> LENGTH: 35
<212> TYPE: DNA
<213> ORGANISM: Artificial Sequence
<220> FEATURE:
<223> OTHER INFORMATION: pGEMCdtBH274Q Primer 1

<400> SEQUENCE: 13
caaattacat ccgatcagtt tcctgttagt tttgt 35

<210> SEQ ID NO 14
<211> LENGTH: 35
<212> TYPE: DNA
<213> ORGANISM: Artificial Sequence
<220> FEATURE:
<223> OTHER INFORMATION: pGEMCdtBH274Q Primer 2

<400> SEQUENCE: 14
acaaaactaa caggaaactg atcggatgta atttg 35

<210> SEQ ID NO 15
<211> LENGTH: 34
<212> TYPE: DNA
<213> ORGANISM: Artificial Sequence
<220> FEATURE:
<223> OTHER INFORMATION: pGEMCdtBR117A Primer 1

<400> SEQUENCE: 15
gatgttgggg caaacgcagt gaacttagct atcg 34

<210> SEQ ID NO 16
<211> LENGTH: 34
<212> TYPE: DNA
<213> ORGANISM: Artificial Sequence
<220> FEATURE:
<223> OTHER INFORMATION: pGEMCdtBR117A Primer 2

<400> SEQUENCE: 16
cgatagctaa gttcactgcg tttgccccaa catc 34

<210> SEQ ID NO 17
<211> LENGTH: 33
<212> TYPE: DNA
<213> ORGANISM: Artificial Sequence
<220> FEATURE:
<223> OTHER INFORMATION: pGEMCdtBD199S Primer 1

<400> SEQUENCE: 17
gatggttgtt ggtagtttca atcgtgcgcc ggt 33

<210> SEQ ID NO 18
<211> LENGTH: 33
<212> TYPE: DNA
<213> ORGANISM: Artificial Sequence
<220> FEATURE:
<223> OTHER INFORMATION: pGEMCdtBD199S Primer 2

-continued

```
<400> SEQUENCE: 18

accggcgcac gattgaaact accaacaacc atc                                33


<210> SEQ ID NO 19
<211> LENGTH: 36
<212> TYPE: DNA
<213> ORGANISM: Artificial Sequence
<220> FEATURE:
<223> OTHER INFORMATION: pGEMCdtBA163R Primer 1

<400> SEQUENCE: 19

cagtgcatgc tttgcgcaca ggtggttctg atgcgg                             36


<210> SEQ ID NO 20
<211> LENGTH: 36
<212> TYPE: DNA
<213> ORGANISM: Artificial Sequence
<220> FEATURE:
<223> OTHER INFORMATION: pGEMCdtBA163R Primer 2

<400> SEQUENCE: 20

ccgcatcaga accacctgtg cgcaaagcat gcactg                             36


<210> SEQ ID NO 21
<211> LENGTH: 36
<212> TYPE: DNA
<213> ORGANISM: Artificial Sequence
<220> FEATURE:
<223> OTHER INFORMATION: pGEMCdtBA163N Primer 1

<400> SEQUENCE: 21

cagtgcatgc tttgaacaca ggtggttctg atgcgg                             36


<210> SEQ ID NO 22
<211> LENGTH: 36
<212> TYPE: DNA
<213> ORGANISM: Artificial Sequence
<220> FEATURE:
<223> OTHER INFORMATION: pGEMCdtBA163N Primer 2

<400> SEQUENCE: 22

ccgcatcaga accacctgtg ttcaaagcat gcactg                             36
```